United States Patent [19]

Niwano et al.

[11] Patent Number: 5,446,124
[45] Date of Patent: Aug. 29, 1995

[54] AROMATIC OLIGOMER AND PROCESS FOR PREPARING THE SAME

[75] Inventors: Masahiro Niwano; Kenji Manabe; Itaru Nitta, all of Tsukuba; Kuniaki Asai, Tondabayashi; Makoto Namioka, Tsukuba; Nobuko Nakayama, both of Tsukuba, all of Japan

[73] Assignee: Sumitomo Chemical Company, Limited, Osaka, Japan

[21] Appl. No.: 920,386

[22] PCT Filed: Dec. 6, 1990

[86] PCT No.: PCT/JP90/01593

§ 371 Date: Aug. 18, 1992

§ 102(e) Date: Aug. 18, 1992

[87] PCT Pub. No.: WO91/12227

PCT Pub. Date: Aug. 22, 1991

[30] Foreign Application Priority Data

Feb. 19, 1990 [JP] Japan .................... 2-039448
Jun. 4, 1990 [JP] Japan .................... 2-14651
Nov. 29, 1990 [JP] Japan .................... 2-334273

[51] Int. Cl.$^6$ ............................... C08G 63/06
[52] U.S. Cl. ............................ 528/361; 528/360
[58] Field of Search .................... 528/360, 361

[56] References Cited

U.S. PATENT DOCUMENTS 3,306,914  2/1967  McNelis .................... 549/280
4,245,084  1/1981  Choe et al. ................ 528/293

FOREIGN PATENT DOCUMENTS 0287233  10/1988  European Pat. Off. .
0331312   9/1989  European Pat. Off. .
0396955  11/1990  European Pat. Off. .
01170618  7/1989  Japan .

OTHER PUBLICATIONS

H. Kricheldorf, "New Polymer Synthesis," *Makromol. Chem.* 184, 475–496 (1983).
Journal of Polymer Science: Part A: Polymer Chemistry, vol. 25, 1987, New York, U.S., pp. 1109–1125—F Jones et al "Graft copolymers of para-hydroxybenzoic acid (PHB)". I. A general method for grafting mesogenic olio—PHB to oligomers.
Database WPI, Week 8609, Derwent Publications Ltd., London, GB; AN 86-059719 & JP-A-61 012 726 (Teijin). *Abstract*
Chemical Abstracts, vol. 78, No. 13, 2 Apr. 1973, Columbus, Ohio, U.S.; Abstract No. 84051, p. 405, column 2 *Abstract* & JP-A-72 038 946 (Sumitomo).
Organische Chemie, A. Streitwieser, Jr. and C. H. Heathcock, Verlag Chemie, Weilheim, 1980, p. 1182.

*Primary Examiner*—James J. Seidleck
*Assistant Examiner*—T. Mosley
*Attorney, Agent, or Firm*—Stevens, Davis, Miller & Mosher

[57] ABSTRACT

The present invention provides an aromatic oligomer comprising repeating structural units represented by the following formula (I), which oligomer has a number-average degree of polymerization of 2 to 10 and a flow temperature of 100° to 400° C.; and a process for preparing the same:

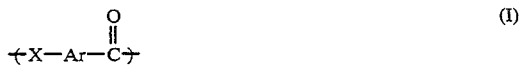

wherein X is selected from O and S; and Ar is selected from

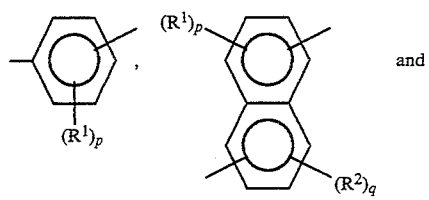

(Abstract continued on next page.)

-continued

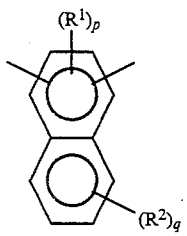

wherein R¹ and R² are each selected from alkyl group having 1 to 3 carbon atoms and phenyl group, and p and q are each an integer of 0 to 2.

The aromatic oligomer of this invention is mixed or reacted with a polymeric substance such as thermoplastic resin, thermosetting resin and rubber to realize enhancement of performance and functional characteristics of the polymeric material.

9 Claims, No Drawings

AROMATIC OLIGOMER AND PROCESS FOR PREPARING THE SAME

FIELD OF ART

The Present invention relates to an aromatic oligomer which is mixed or reacted with polymeric materials such as thermoplastic resins, thermosetting resins and rubbers to realize enhancement of performance and functional characteristics of said polymeric materials, and a process for preparing such an aromatic oligomer.

BACKGROUND ART

Recent progress of technology in various fields of industries such as electric and electronic field, fields of office automation (OA) and audiovisual (AV) devices, automobile industries, etc., is amazing, and the polymeric materials used in these new fields of art are required to have high performance such as high strength and high thermal resistance that could not be realized with the conventional polymeric materials and the excellent functions such as those of a thermoplastic elastomer with excellent thermal resistance that could not be attained with the conventional polymeric materials.

Request for such high performance and enhanced functional characteristics has been dealt with by various methods in the respective fields of application. For instance, in the case of thermoplastic resins, strenuous studies have been made on the development of condensation type polymers represented by engineering plastic, development of whole aromatic polymers, blending of these polymeric materials, etc. In the case of thermosetting resins, too, similar studies have been made in accordance with the field of use.

Presently, as thermoplastic elastomer (hereinafter referred to as "TPE"), TPE's comprising block copolymers composed of soft segments and hard segments are widely used.

As such TPE, there are known the block copolymers called polyester elastomers consisting of the aliphatic polyether portion such as polytetramethylene glycol and the polyester portion such as polyethylene terephthalate and polybutylene terephthalate, and the block copolymers called polyamide elastomers consisting of the aliphatic polyether portion and the polyamide portion such as polydodecalactum. It is considered that in these block copolymers, each of the hard segments constitutes a micro-domain structure, which plays the role of physical crosslinking point to provide rubber elasticity to said copolymers.

European Patent Laid-Open Specification 0287233 discloses preparation of a polymer solution for coating from a copolymer having an aromatic polyester as side chain, that is, a copolymer having an aromatic polymer covalently bonded to an acrylic or polyester resin, said polymer solution being claimed to be capable of forming a coating film with high hardness. This patent specification, however, is silent on the aromatic oligomer of the present invention.

Further, the whole aromatic polyesters, such as polyhydroxybenzoic acid, are the polymers with excellent thermal resistance but the scope of their use is limited due to the problems that they are not thermoplastic, that they are insoluble in solvents, etc. It is tried, therefore, to lower the melting temperature by random copolymerization with other copolymerizable monomers or to improve solubility in solvents.

However, studies of these polymeric materials with high performance and high functional ability from the stage of synthesis require a long time and also involve many economical problems. Also, in certain fields of use, the two conflicting properties, viz. high thermal resistance and excellent moldability, are required at the same time, but it is hard to develop a polymeric material which can satisfy this requirement. Further, attempts have been made to realize high performance by blending the polymeric materials, but in many cases such attempts would fail to attain the target performance due to the reasons such as difficulty of morphological control.

In TPE comprising a copolymer composed of soft segments and hard segments, the ratio of the hard segments needs to be not less than several 10% by weight for allowing them to constitute a micro-domain structure and play the role of physical crosslinking point. Also, these TPE are large in compression set (100° C., 70 hr) and not so high in thermal resistance. This is because the hard segment itself does not have high thermal resistance.

Further, there is yet available no report on use of an aromatic polyester as starting material of TPE by lowering the molecular weight of the polyester to make it fusible.

DISCLOSURE OF THE INVENTION

In order to solve said problems, the present inventors have made persistent studies for the development of modifying agent for polymeric materials having better performance than the conventional agents and, as a result, found that an aromatic oligomer having a specific average degree of polymerization and a specific flow temperature and composed of specific repeating units is very useful as a modifying agent for polymeric materials, and this finding has led to the attainment of the present invention.

Thus, the present invention relates to an aromatic oligomer characterized in that it is composed of the repeating units represented by the following formula (I) and that the number-average degree of polymerization is 2–10 and the flow temperature defined below is 100°–400° C.; and a process for preparing such an aromatic oligomer:

(wherein X is selected from O and S, and the structural units containing O and the structural units containing S may be both contained in one oligomer; and Ar is selected from

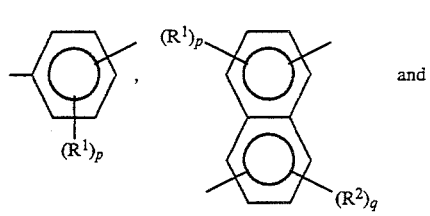

-continued

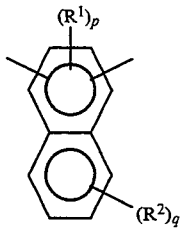

wherein $R^1$ and $R^2$ are each selected from alkyl group having 1-3 carbon atoms and phenyl group, but $R^1$ and $R^2$ may be a same or different groups, and the different groups may be attached to one benzene ring; p and q are each an integer of 0-2);

flow temperature: the temperature at which the melt viscosity (of the aromatic oligomer) reaches 48,000 poises when the oligomer is melted by heating at a rate of 4° C./min and extruded from a nozzle of 1 mm in inner diameter and 10 mm in length under a load of 100 kg/cm².

Further, the aromatic oligomer of this invention is preferably the one in which the sum of the monomer content and the dimer content is not greater than 5% by weight.

A typical example of such aromatic oligomer is the one represented by the following formula:

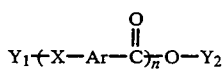

(wherein X and Ar are the same as those in formula (I); $Y_1$ is selected from hydrogen, benzoyl group and lower alkanoyl group; $Y_2$ is selected from hydrogen, halogen, benzyl group, lower alkyl group and phenyl group substituted with lower alkyl; and n is 3-10 on a number average).

The number-average molecular weight of the aromatic oligomer of this invention is preferably in the range of 300-1,500, more preferably in the range of 400-1,000. If the number-average molecular weight is less than 300, said polycondensate becomes susceptible to thermal decomposition and is also excessively lowered in flow temperature, resulting in a reduction of thermal resistance of the obtained resin composition or graft copolymer. On the other hand, if said number-average molecular weight exceeds 1,500, the flow temperature approaches the thermal decomposition temperature of said oligomer, causing deterioration of moldability of the obtained resin composition or graft copolymer.

Said oligomer, for control of its properties such as melting point, may contain a structure in which a monomer such as hydroxyalkylcarboxylic acid, aminoalkylcarboxylic acid, aminoarylcarboxylic acid or the like is polycondensed and a structure in which a monofunctional carboxylic compound, a phenol compound and an amino compound are condensed.

It is especially preferred that said repeating structural units of said aromatic oligomer consist of

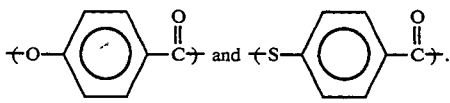

(Hereinafter, the repeating structural unit of

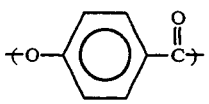

is referred to as POB structural unit.)

The present invention further provides a method for efficiently removing the monomer and dimer alone from the aromatic oligomer in which monomer and dimer stay mixed. That is, said aromatic oligomer is washed with a polar solvent inert to said oligomer, whereby monomer and dimer alone can be removed efficiently.

Regarding the aromatic oligomers having POB structural units, mention is made of such oligomers in Japanese Patent Publication Nos. 6796/71 and 27415/74, Japanese Patent Application Kokai (Laid-Open) Nos. 4722/87, 137950/88, 170618/89 and 185322/89, Die Makro-molekulare Chemie, Vol. 184, pp. 475-496 (1983), and Journal of Poller Science: Part A: Poller chemistry, Vol. 25, pp. 1109-1125 (1987), but none of these publications is suggestive of the present invention.

The aromatic oligomer of this invention is an oligomer containing 50 wt % or more, preferably 60 wt % or more of the repeating structural units represented by the above-shown formula (I).

The number-average degree of polymerization of the aromatic oligomer according to this invention is 2-10, preferably 3-8, more preferably 4-7. If the number-average degree of polymerization is greater than 10, said oligomer becomes highly crystalline and won't be melted even when heated. If the oligomer is not melted, good mixing of a polymeric material and said oligomer can not be expected when they are mixed, and in case a polymeric material and said oligomer are reacted, the reaction rate is very low or there takes place no reaction at all. For allowing said oligomer to melt in a favorable way, it is necessary that the number-average degree of polymerization of said oligomer is less than 10, preferably less than 8. From the viewpoint of thermal stability, it is desirable that the number-average degree of polymerization of said oligomer is higher than 3. Since said oligomer is soluble only in certain specific solvents such as 2,3,5,6-tetrafluorophenol, the number-average polymerization degree of said oligomer can not be measured by an ordinary method such as vapor pressure osmometry. Also, since the degree of polymerization of said oligomer is low, its weight-average degree of polymerization can not be measured by an ordinary method such as light scattering method. However, the average degree of polymerization of said oligomer can be determined absolutely by gel permeation chromatography. That is, the average degree of polymerization can be determined from the peak area of each degree of polymerization on the chromatogram of said oligomer. Also, presence or absence and the amounts present of the monomer and dimer can be confirmed by high performance liquid chromatography.

The aromatic oligomer of this invention has a flow temperature, defined below, of 100° C. or above, preferably 150° C. or above, more preferably 170° C. or above. Also, the flow temperature of said aromatic oligomer should not be higher than 400° C., preferably not higher than 350° C., more preferably not higher than 300° C., most preferably 170°–300° C.

Flow temperature: the temperature at which the melt viscosity of the aromatic oligomer reaches 48,000 poises when the oligomer melted by heating at a rate of 4° C./min is extruded from a nozzle of 1 mm in inner diameter and 10 mm in length under a load of 100 kg/cm$^2$.

For realizing enhancement of performance of a polymeric material by using the aromatic oligomer of this invention, it is desirable that said oligomer shows liquid crystallinity in the molten state. In consideration of thermal stability of the polymeric material, the aromatic oligomer of this invention is preferably the one which shows melt liquid crystallinity at a temperature in the range of 130°–470° C., preferably 170°–400° C.

Further, said oligomer of this invention is preferably the one in which the sum of the contents of monomer and dimer is less than 5% by weight, more preferably less than 3% by weight. In the synthesis of aromatic oligomers with the prior art, it was impossible to selectively obtain those with uniform polymerization degree, and there would remain monomer and/or dimer in the obtained oligomers. The amount of monomer and dimer remaining in the produced oligomers would be at least 8% by weight, and they could, for instance, exist in as much an amount as 13% by weight in the oligomer. However, presence of monomer and dimer in the oligomers is undesirable as it becomes a cause of troubles such as foaming at the time of mixing with polymeric substances.

In view of the above, the present inventors have tried washing with various types of solvents for the purpose of removing monomer and dimer and, as a result, found that the polar solvents inert to the aromatic oligomers can best selectively extract monomer and dimer.

Both molecular terminals of said aromatic oligomers should be selected by taking into account the polymeric material to be added with said oligomer, purpose of addition of said oligomer and economy. Thus, in case of preparing a resin composition by adding said oligomer to a resin, both molecular terminals of said oligomer preferably carry a group inert to the resin added.

In case of producing a thermoplastic graft copolymer by grafting said aromatic oligomer to a polymer having a glass transition temperature of 10° C. or below, one terminal of said oligomer comprises a functional group reactable with said polymer while the other terminal comprises an inert group.

More specifically, the aromatic oligomers of this invention include those having at their molecular terminals hydrogen, an aliphatic or aromatic hydrocarbon group such as alkyl group, aryl group, etc., or a group derived therefrom; those having at their molecular terminals a halogen atom, a group having a halogen, such as halide group, or a group derived therefrom; those having at their molecular terminals a group having oxygen such as hydroxyl group, aldehyde group, ketone group, epoxy group, acyl group, carboxyl group, halogenated acyl group, acid anhydride group, ester group, peracid group, etc., or a group derived therefrom; those having at their molecular terminals a group having nitrogen such as amino group, acid amide group, acid imide group, nitrile group, isonitrile group, isocyanate group, etc., or a group derived therefrom; those having at their molecular terminals a heterocyclic group or a group derived therefrom; and those having at their molecular terminals a group having sulfur, phosphorus, silicon or the like, or a group derived therefrom; and the like.

These end groups can be introduced by such a method as modifying the end groups after synthesizing said oligomer or using a monomer having the objective end groups as reaction terminator. As the oligomers are low in molecular weight, these end groups can be confirmed by an ordinary method such as IR spectrum.

Further, if necessary, it is possible to use an oligomer which has undergone nuclear substitution. The groups to be introduced by nuclear substitution are not specified. The nuclear substituent groups should be selected by taking into consideration the polymeric material to which said oligomer is added, purpose of addition of said oligomer and economy. Concretely, the groups such as mentioned above can be named as examples of said nuclear substituent groups. Introduction of these substituents can be accomplished, for example, by conducting nuclear substitution after the synthesis of said oligomer or using a monomer which has undergone nuclear substitution.

As the method for preparing an aromatic oligomer according to this invention, there can be cited a method characterized in that a hydroxyarylcarboxylic acid and/or a mercaptoarylcarboxylic acid are acetylated, then acetic acid is distilled away and the hydroxyarylcarboxylic acid and/or mercaptoarylcarboxylic acid and an terminal-stopped monomer are reacted when ester exchange reaction is performed.

There can also be mentioned a method characterized in that a hydroxyarylcarboxylic acid and/or a mercaptoarylcarboxylic acid are acetylated, then the produced acetic acid is distilled away, and when ester exchange reaction is performed, the amount of acetic acid distilled away is measured to calculate the polymerization degree of the produced oligomer, and the ester exchange reaction is stopped when the desired polymerization degree is reached.

There can further be mentioned a method characterized in that (a) a hydroxyarylcarboxylic acid and/or a mercaptoarylcarboxylic acid and (b) a carboxylic acid selected from the group consisting of alkylcarboxylic acids having 5 or more carbon atoms, arylcarboxylic acids having 7 or more carbon atoms and aralkylcarboxylic acids are used as starting materials, and the hydroxyarylcarboxylic acid and/or mercaptoarylcarboxylic acid are acetylated with acetic anhydride, then acetic acid is distilled away and thereafter ester exchange reaction is carried out.

There can also be mentioned a method characterized in that (a) a hydroxyarylcarboxylic acid and/or a mercaptoarylcarboxylic acid and (b) a compound selected from the group consisting of alkylcarboxylic acids, arylcarboxylic acids and aralkylcarboxylic acids having 5 or more carbon atoms and possessing at one terminal of the molecule a functional group selected from the group consisting of halogen atom, alkylsilylether group, silyl halide group, acetic anhydride group and a group having an unsaturated double bond are used as starting materials, and which comprises acetylating the hydroxyl groups and/or mercapto groups in the starting materials by acetic anhydride, then distilling away acetic acid and conducting an ester exchange reaction.

There can further be mentioned a method characterized by using, as starting materials, (a) a hydroxyarylcarboxylic acid and/or a mercaptoarylcarboxylic acid and (b) a compound selected from the group consisting of alkyl alcohol of 5 or more carbon atoms, alkylthiol of 5 or more carbon atoms, aryl alcohol, arylthiol, aralkyl alcohol and aralkylthiol and having at one terminal of the molecule a functional group selected from the group consisting of halogen atom, alkylsilyl ether group, silyl halide group, acid anhydride group and a group-having an unsaturated double bond, and comprising acetylating the hydroxyl groups and/or mercapto groups in the starting materials by acetic anhydride, distilling away acetic acid and carrying out an ester exchange reaction.

There can additionally be mentioned a method characterized in that a hydroxyarylcarboxylic acid and/or a mercaptoarylcarboxylic acid are reacted with acetic anhydride of a greater number of moles than the total number of moles of said carboxylic acids, the hydroxyl groups and/or mercapto groups are entirely acetylated, acetic acid is distilled away and an ester exchange reaction is carried out, this ester exchange reaction being stopped when 1.5-1.9 times as much number of moles of acetic acid as the total number of moles of said carboxylic acids has been distilled away.

There can further be mentioned a method in which a hydroxyarylcarboxylic acid and/or a mercaptoarylcarboxylic acid are reacted with acetic anhydride of 0.5-0.9 times the total number of moles of said carboxylic acids, the hydroxyl groups and/or mercapto groups are acetylated, acetic acid is distilled away and an ester exchange reaction is carried out.

A more detailed description of said methods will be given later.

The aromatic oligomer of this invention is useful as a modifying agent for polymeric materials. Especially, a thermoplastic graft copolymer obtained by grafting, as side chain, an aromatic oligomer of this invention having a flow temperature of 100° C. or above to, as main chain, a polymer having a glass transition temperature of 10° C. or below is very useful as a thermoplastic elastomer with high thermal resistance.

Said thermoplastic graft copolymer can be used as a thermoplastic elastomer which shows rubber elasticity in a wide temperature range above room temperature.

It is considered that the repeating units (I) of said aromatic oligomer function as the hard segments in the obtained graft copolymer and they form a microdomain structure which constitutes the physical crosslinking points.

It is supposed that usefulness of the obtained graft copolymer as a thermoplastic elastomer having excellent thermal resistance is attributable to the above-said reason. This supposition, however, is in no way restrictive to this invention.

The polymer having Tg of 10° C. or below, however, should be 50-99% by weight, preferably 65-97% by weight of the whole polymer. If the proportion of the polymer having Tg of 10° C. or below is less than 50% by weight of the whole polymer, the obtained thermoplastic elastomer may fail to show enough rubber elasticity in the temperature range above the glass transition temperature. If the proportion of the polymer having Tg of 10° C. or below exceeds 99% by weight of the whole polymer, the physical crosslinking points in the side chain will be so lessened in number as to make the obtained polymer liable to suffer excessive plastic deformation even at room temperature.

The combination of the reactive functional group in the main chain and the functional group in the side chain reactable with the reactive functional group in the main chain can be properly selected according to the purpose of use of the produced elastomer.

As for the method for preparing said thermoplastic graft copolymer, there can be mentioned, for example, a method in which a polymer having a glass transition temperature of 10° C. or below and possessing a functional group reactable with carboxyl group is reacted with an aromatic oligomer of this invention having a flow temperature of 100° C. and possessing a carboxyl group at one end of the molecule.

There can be also mentioned a method in which a polymer having a glass transition temperature of 10° C. or below and possessing a functional group reactable with acid anhydride group is reacted with an aromatic oligomer of this invention having a flow temperature of 100° C. or above and possessing an acid anhydride group at one end of the molecule.

There can further be mentioned a method in which a polymer having a glass transition temperature of 10° C. or below and also having radical reactivity is reacted with an aromatic oligomer of this invention having a flow temperature of 100° C. or above and possessing a functional group having radical reactivity at one end of the molecule.

There can also be mentioned a method in which a polymer having a glass transition temperature of 10° C. or below and also having unsaturated double bonds in its structure is reacted with an aromatic oligomer of this invention having a flow temperature of 100° C. or above and possessing, at one end of the molecule, a functional group reactable with the unsaturated double bonds.

There can further be mentioned a method in which an organopolysiloxane having a glass transition temperature of 10° C. or below and partly modified with a reactive functional group is reacted with an aromatic oligomer of this invention having a flow temperature of 100° C. or above and possessing, at one end of its molecule, a functional group reactable with the functional group in said polysiloxane.

Hereinbelow, the methods for preparing a thermoplastic graft copolymer by using an aromatic oligomer of this invention will be described in further detail.

As a method for preparing a thermoplastic graft copolymer by using an aromatic oligomer of this invention, there can be mentioned a method in which a polymer having a glass transition temperature of 10° C. or below and possessing a functional group reactable with carboxyl group is reacted with an aromatic oligomer having a flow temperature of 100° C. or above and possessing a carboxyl group at one terminal of the molecule. Preferred examples of the functional groups reactable with carboxyl group are glycidyl group, epoxy group, isocyanate group, hydroxyl group and acetoxyl group. Glycidyl group and epoxy group are especially preferred.

As said polymers containing glycidyl group and/or epoxy group, there can be cited the following copolymers: methyl acrylate-glycidyl methacrylate copolymer, ethyl acrylate-glycidyl methacrylate copolymer, propyl acrylate-glycidyl methacrylate copolymer, butyl acrylate-glycidyl methacrylate copolymer, hexyl acrylate-glycidyl methacrylate copolymer, dodecyl acrylate-glycidyl methacrylate copolymer, methyl acrylate-glycidylstyrene copolymer, ethyl acrylate-glycidylstyrene copolymer, propyl acrylate-glycidylstyrene copolymer, butyl acrylate-glycidylstyrene copolymer, hexyl acrylate-glycidylstyrene copolymer, dodecyl acrylate-glycidylstyrene copolymer, methyl acrylate-N-[4-(2,3-epoxypropoxy)-3,5-dimethyl]acrylamide copolymer, ethyl acrylate-N-[4-(2,3-epoxypropoxyl)-3,5-dimethylbenzyl]acrylamide copolymer, propyl acrylate-N-[4-(2,3-epoxypropoxy)-3,5-dimethylbenzyl]acrylamide copolymer, butyl acrylate-N-[4-(2,3-epoxypropoxy)-3,5dimethylbenzyl]acrylamide copolymer, hexyl acrylate-N-[4-(2,3-epoxypropoxy)-3,5-dimethylbenzyl]acrylamide copolymer, dodecyl acrylate-N-[4-(2,3-epoxypropoxy)-3,5-dimethylbenzyl]acrylamide copolymer, acrylonitrile-butadiene-glycidyl methacrylate terpolymer, acrylonitrile-butadiene-glycidylstyrene terpolymer, acrylonitrile-butadiene-N-[4-(2,3-epoxypropoxy)-3,5-dimethylbenzyl]acrylamide terpolymer, ethylene-vinyl acetate-glycidyl methacrylate terpolymer, ethylene-vinyl acetate-glycidylstyrene terpolymer, ethylene-vinyl acetate-N-[4-(2,3-epoxypropoxy)-3,5-dimethylbenzyl]acrylamide terpolymer, ethylene-methyl acrylate-glycidyl methacrylate terpolymer, ethylene-ethyl acrylate-glycidyl methacrylate terpolymer, ethylene-propyl acrylate-glycidyl methacrylate terpolymer, ethylene-butyl acrylate-glycidyl methacrylate terpolymer, ethylene-hexyl acrylate-glycidyl methacrylate terpolymer, ethylene-dodecyl acrylate-glycidyl methacrylate terpolymer, ethylene-methyl acrylate-glycidylstyrene terpolymer, ethylene-ethyl acrylate-glycidylstyrene terpolymer, ethylene-propyl acrylate-glycidylstyrene terpolymer, ethylene-butyl acrylate-glycidylstyrene terpolymer, ethylene-hexyl acrylate-glycidylstyrene terpolymer, ethylene-dodecyl acrylate-glycidylstyrene terpolymer, ethylene-methyl acrylate-N-[4-(2,3-epoxypropoxy)-3,5-dimethylbenzyl]acrylamide terpolymer, ethylene-ethyl acrylate-N-[4-(2,3-epoxypropoxy)-3,5-dimethylbenzyl]acrylamide terpolymer, ethylene-propyl acrylate-N-[4-(2,3-epoxypropoxy)-3,5-dimethylbenzyl]acrylamide terpolymer, ethylene-butyl acrylate-N-[4-(2,3-epoxypropoxy)-3,5-dimethylbenzyl]acrylamide terpolymer, ethylene-hexyl acrylate-N-[4-(2,3-epoxypropoxy)-3,5-dimethylbenzyl]acrylamide terpolymer, ethylene-dodecyl acrylate-N-[4-(2,3-epoxypropoxy)-3,5-dimethylbenzyl]acrylamide terpolymer, styrene-butadiene-glycidyl methacrylate terpolymer, styrene-butadiene-glycidylstyrene terpolymer, and styrene-butadiene-N-[4-(2,3-epoxypropoxy)-3,5-dimethylbenzyl]acrylamide terpolymer. These copolymers can be obtained by generally known radical polymerization. Organopolysiloxanes having epoxy group and/or glycidyl group in the side chain can also be mentioned as said polymers.

Also, double bonds in a polymer having the double bonds may be epoxidated by a known method, for example, the method shown in U.S. Pat. No. 3,155,638, to use said polymer as main chain of the thermoplastic graft copolymer.

For example, a method can be mentioned in which a peracid such as m-chloroperbenzoic acid is acted to a toluene solution of an ethylene-propylene-diene monomer terpolymer (hereinafter referred to as EPDM).

Introduction of glycidyl group into the polymer having double bonds can be effectuated by various methods. For example, it is possible to effect grafting by polymerization of a monomer having polymerizable double bonds and glycidyl group, such as glycidyl methacrylate, allylglycidyl ether or glycidyl acrylate, in a suitable organic solvent in the presence of EPDM, or by copolymerization of said monomer and another monomer copolymerizable therewith, such as butyl acrylate.

The aromatic oligomer having a flow temperature of 100° C. or above, preferably 150° C. or above, and possessing a carboxyl group at one terminal of the molecule, which is used in the present invention, is preferably the one represented by the following formula (II):

(wherein X is selected from O and S, and the structural units containing O and the structural units containing S may be both contained in one oligomer; $R^{10}$ is an alkyl group having 5 or more carbon atoms or an aryl or aralkyl group having 6 or more carbon atoms; Ar is selected from

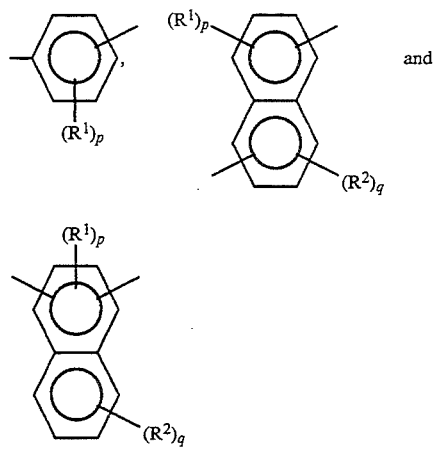

wherein $R^1$ and $R^2$ are each selected from an alkyl group having 1-3 carbon atoms and a phenyl group; $R^1$ and $R^2$ may be a same or different groups, and the different substituents may be attached to the same benzene ring; p and q are each an integer of 0-2; and n is 2-10 on a number average).

A hydroxycarboxylic acid having 2-6 carbon atoms may be copolymerized with said oligomer. The number-average molecular weight of the aromatic oligomer having a carboxyl group at one terminal of the molecule shown above is preferably within the range of 300-1,500. n is a mean value, which is a number in the range of 2-10 determined according to what are selected for $R^{10}$, $R^1$, $R^2$ and Ar. n is preferably a number in the range of 3-8, more preferably 4-7.

The hydroxyarylcarboxylic acid polymer can be obtained by any method provided that it is capable of producing a polycondensate by using as starting material hydroxyarylcarboxylic acid and, in some cases, a small quantity of a copolymerizable monomer such as $C_{2-6}$ hydroxyalkylcarboxylic acid, aminoalkylcarboxylic acid, aminoarylcarboxylic acid, monofunctional phenol compound, carboxylic acid compound, amino compound and the like, but it is preferred to prepare said polymer by the following method. This method can be also applied for the preparation of mercaptoarylcarboxylic acid polymer.

That is, an acetylating agent such as acetic anhydride or acetyl chloride is added to hydroxyarylcarboxylic acid and the mixture is heated and stirred to obtain acetoxyarylcarboxylic acid. In the above reaction, in case of acetylating hydroxyarylcarboxylic acid, etc. with acetic anhydride, acetylation can be accomplished by conducting the reaction at 100° C. or above for a period of 15 minutes or more, and in the case of the reaction using acetyl chloride, acetylation can be attained by performing the reaction at room temperature or above for a period of 30 minutes or more. In either case, it is recommendable that acetic anhydride or acetyl chloride be added in an excess amount, preferably in an amount of 1.1 mole to 1 mole of the hydroxyl group to be reacted. After completion of acetylation, the reaction system is now deacetylated while heating and stirring the system to allow progress of the polycondensation reaction. The system temperature needs to be kept preferably at or above 200° C. The number-average molecular weight can be controlled by adjusting the amount of acetic acid distilled away. For controlling the degree of polymerization at the desired level, it is necessary to calculate the amount of the monomer fed such as hydroxyarylcarboxylic acid and the amount of acetic acid to be distilled away.

For the preparation of the aromatic oligomer having a carboxyl group at one terminal of the molecule, a mixture of a monocarboxylic acid having an alkyl group of 5 or more, preferably 5-20 carbon atoms, and an aryl group of 6 or more, preferably 6-14 carbon atoms, hydroxyarylcarboxylic acid and if necessary hydroxycarboxylic acid of 2-6 carbon atoms is acetylated with acetic anhydride or acetyl chloride and then deacetylated in the same way as above-described preparation of hydroxyarylcarboxylic acid polymer to give a polycondensate. In this reaction, the number-average molecular weight is determined by the molar ratio of monocarboxylic acid to hydroxycarboxylic acid.

Further, the obtained aromatic oligomer is preferably washed under stirring with a solvent selected from methanol, ethanol and acetone and then filtered. By these operations, the monomer and dimer contained in the aromatic oligomer after polycondensation are selectively washed away to improve thermal stability of the aromatic oligomer.

Especially by washing the aromatic oligomer containing the monomer and dimer with methanol, it is possible to remove the monomer and dimer to a great extent. More specifically, methanol washing can reduce the content of monomer and dimer in the aromatic oligomer to less than 5% by weight, preferably less than 3% by weight, more preferably less than 1% by weight.

It is especially noteworthy that it has become possible to easily reduce the content of monomer and dimer to less than 1% by weight, that is, to substantially remove monomer and dimer, by methanol washing.

The content of monomer and dimer can be adjusted by changing the degree of washing with methanol or by conducting washing with a mixed solution of methanol and other suitable solvent (e.g. water).

As the method for washing with methanol, there can be mentioned a method in which the aromatic oligomer is added with 1-20 times, preferably 2-10 times (by weight) as much amount of methanol and the mixture is stirred under methanol refluxing for 10 minutes to 2 hours, preferably 20 minutes to one hour, and then filtered with the temperature kept at 30°-60° C., and the formed cakes are recovered and dried. A method can be also mentioned in which washing is performed by using an appropriate apparatus, typically a Soxhlet extractor.

The thermoplastic graft copolymer can be obtained by reacting a polymer which has a Tg of 10° C. or below and a functional group reactable with carboxyl group and an aromatic oligomer of this invention having a flow temperature of 100° C. or above and possessing a carboxyl group at one terminal of the molecule. The reaction method is not specifically defined, but a method in which the reaction is effected by melt mixing is preferred.

This melt mixing can be accomplished by using any mixing apparatus provided that it is capable of exerting high shearing force to said polymer having Tg of 10° C. or below and an aromatic oligomer of this invention at high temperature above the flow temperature of said aromatic oligomer, for example such ordinarily used mixing machines as Banbury mixer, single-screw extruder, twin-screw extruder, roll mill, kneader and the like.

Reaction temperature is preferably above the flow temperature of the aromatic oligomer of this invention and below the thermal decomposition temperature of said polymer having Tg of 10° C. or below used. If the reaction temperature is below the flow temperature of the aromatic oligomer used, the reaction between the carboxylic acid of said aromatic oligomer and the polymer having Tg of 10° C. or below is retarded, making it difficult to obtain the desired graft copolymer. If the reaction temperature exceeds the thermal decomposition temperature of the polymer having Tg of 10° C. or below, there takes place considerable decomposition of said polymer in the course of mixing, causing bad effects such as decrease of molecular weight.

For promoting grafting, it is desirable that the temperature is as high as possible within the above-defined temperature range, the reaction time is as long as possible, and the shearing force is as large as possible. For further accelerating grafting, it is recommended to add a phosphine catalyst, a tertiary amine or like material.

Next, as the method for preparing the thermoplastic graft copolymer, there can be mentioned a method in which a polymer having a glass transition temperature of 10° C. or below and possessing a functional group reactable with acid anhydride group is reacted with an aromatic oligomer of this invention having a flow temperature of 100° C. or above and possessing an acid anhydride group at one terminal of the molecule.

As the functional group reactable with acid anhydride group, there can be mentioned glycidyl group, epoxy group, amino group and the like.

As the polymer containing glycidyl group and/or epoxy group, there can be mentioned here again the polymer containing epoxy group and/or glycidyl group reactable with the aromatic oligomers having a carboxyl group at one terminal of the molecule, which have been mentioned before. That is, there can be mentioned the afore-cited various kinds of copolymers prepared from copolymerization of glycidyl methacrylate, glycidylstyrene, allylglycidyl ether and the like. There can further be mentioned the polymers obtained by epoxidating the double bonds of the polymers having double bonds; and the organopolysiloxanes having glycidyl group and/or epoxy group in the side chain; and the like.

Further, as the polymers having amino group, there can be mentioned various kinds of copolymers prepared from copolymerization of monomers having unsaturated double bond and amino group in the same molecule, such as aminostyrene, allylamine, etc., and various kinds of polymers modified by grafting said monomers to the side chain.

The aromatic oligomers of this invention having a flow temperature of 100° C. or above, preferably 150° C. or above, and possessing an acid anhydride group at one terminal of the molecule are preferably ones represented by the following formula (III):

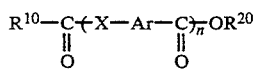
(III)

(wherein X is selected from O and S, and the structural units containing O and the structural units containing S may both be contained in one oligomer; when $R^{10}$ is

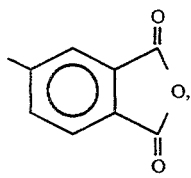

$R^{20}$ is selected from hydrogen, alkyl group of 1–10 carbon atoms and aryl group of 6–20 carbon atoms, and when $R^{20}$ is

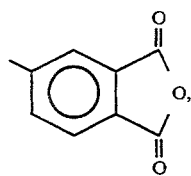

$R^{10}$ is selected from alkyl group of 1–10 carbon atoms and aryl group of 6–20 carbon atoms; Ar is selected from

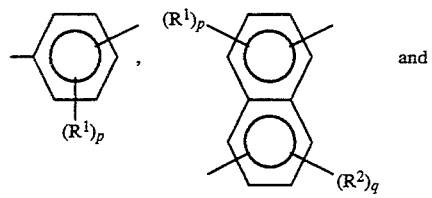
and
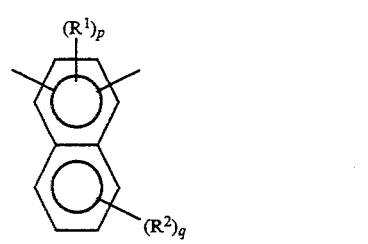

wherein $R^1$ and $R^2$ are each selected from alkyl group of 1–3 carbon atoms and phenyl group; $R^1$ and $R^2$ may be a same or different groups, and the different substituents may be attached to the same benzene ring; p and q are each an integer of 0–2; and n is 2–10 on a number average).

Said aromatic oligomer can be obtained by mixing trimellitic acid anhydride or 4-acetoxyphthalic anhydride and an acetoxyarylcarboxylic acid in a molar ratio of 1:1 to 1:10 and condensing them.

As the acetoxyarylcarboxylic acids usable in this invention, there can be mentioned one obtained by acetylating a hydroxyarylcarboxylic acid having 7 or more, preferably 7–20 carbon atoms. Incidentally, when X is S in the formula (III), it can be prepared in the same way as described above. More specifically, there can be mentioned those represented by the following formulae:

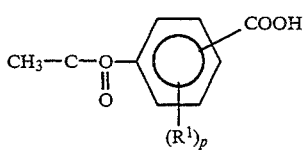

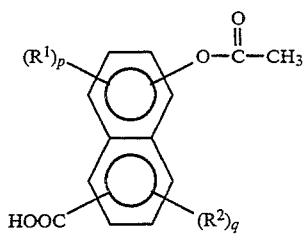

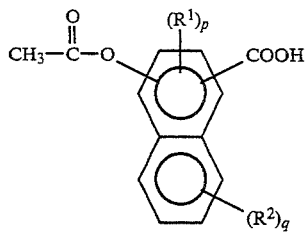

(wherein $R^1$ and $R^2$ are each selected from alkyl group of 1–3 carbon atoms and phenyl group; $R^1$ and $R^2$ may be same or different, and the different substituents may be attached to the same benzene ring; p and q are each an integer of 0–2).

Among them, p-acetoxybenzoic acid is preferably used.

The aromatic oligomers having an acid anhydride at one terminal of the molecule according to this invention can be obtained by distilling away acetic acid from a mixture of trimellitic acid anhydride or 4-acetoxyphthalic anhydride and acetoxyarylcarboxylic acid.

In the above reaction, acetoxyarylcarboxylic acid can be obtained by acetylating hydroxyarylcarboxylic acid with acetic anhydride or acetyl chloride. In case of acetylating hydroxyarylcarboxylic acid with acetic anhydride, acetylation can be accomplished by conducting the reaction at 100° C. or above for a period of 15 minutes or more. In the case of the reaction using acetyl chloride, acetylation can be achieved by performing the reaction at room temperature or above for a period of 30 minutes or more.

In either case, it is desirable that acetic anhydride or acetyl chloride be added in an excess amount, preferably about 1.1 time the molar quantity of the hydroxyl group to be reacted.

After completion of acetylation, trimellitic acid anhydride or 4-acetoxyphthalic anhydride is mixed in the system and acetic acid is distilled away while heating the system with stirring to let the polycondensation reaction proceed on.

The temperature in the system needs to be kept preferably at or above 200° C.

The number-average molecular weight of the aromatic oligomer obtained from this reaction is determined by the molar ratio of hydroxyarylcarboxylic acid to trimellitic acid anhydride or 4-acetoxyphthalic anhydride supplied.

For obtaining a graft copolymer by reacting an aromatic oligomer of this invention with a thermoplastic polymeric material having Tg of 10° C. or below and for forming TPE therefrom, it is desirable that the flow temperature of said aromatic oligomer is 100°–400° C., preferably 150°–350° C., more preferably 170°–300° C., and that trimellitic acid anhydride or acetoxyphthalic anhydride and acetoxyarylcarboxylic acid are mixed in a molar ratio of 1:1 to 1:10, preferably 1:1.5 to 1:8, in effectuating polycondensation.

If acetoxyarylcarboxylic acid is less in molar quantity than trimellitic acid anhydride or acetoxyphthalic anhydride, the obtained aromatic oligomer is low in molecular weight and susceptible to thermal decomposition. Also, the flow temperature of the oligomer lowers considerably, and when such oligomer is used for the hard segments of TPE, the obtained TPE becomes poor in thermal resistance.

When polycondensation is performed by mixing acetoxyarylcarboxylic acid in an amount of more than 10 moles to one mole of trimellitic acid anhydride or acetoxyphthalic anhydride, the flow temperature of the obtained aromatic oligomer exceeds 400° C. and approaches the thermal decomposition temperature of said aromatic oligomer, so that when such oligomer is used for the hard segments of TPE, the obtained TPE is deteriorated in moldability.

Further, it is desirable that the obtained aromatic oligomer, after pulverization, be washed under stirring with a solvent selected from acetone, tetrahydrofuran, N-methylpyrrolidone, chloroform, toluene and pyridine, and then filtered, whereby mainly the monomer and dimer contained in the aromatic oligomer after polycondensation are washed away to improve thermal stability of said aromatic oligomer.

The aromatic oligomers of this invention, namely the aromatic oligomers having an acid anhydride at one terminal of the molecule, can be reacted as a grafting agent with various polymeric materials having a functional group reactable with the acid anhydride to realize enhancement of performance and functional capability of said polymeric materials.

Especially, by reacting said aromatic oligomer with a thermoplastic polymeric material having a glass transition temperature of 10° C. or below and possessing a functional group reactable with acid anhydride, in a ratio by weight of 1:99 to 50:50 to synthesize a graft copolymer, it is possible to produce a thermoplastic elastomer having high thermal resistance.

The method for the above reaction is not specifically defined, but it is preferred to effectuate the reaction by melt mixing.

Next, as the method for preparing a thermoplastic graft copolymer, there can be mentioned a method in which a polymer having a glass transition temperature of 10° C. or below and having radical reactivity is reacted with an aromatic oligomer of this invention having a flow temperature of 100° C. or above and possessing a functional group having radical reactivity at one terminal of the molecule.

As the polymers containing the units having radical reactivity, which are usable in this invention, there can be mentioned ethylene-propylene copolymer, ethylene-propylene-butadiene terpolymer, ethylene-propylene-isoprene terpolymer, ethylene-propylene-1,5-hexadiene terpolymer, ethylene-propylene-methylenenorbornene terpolymer, and ethylene-propylene-ethylidenenorbornene terpolymer.

The aromatic oligomers having a flow temperature of 100° C. or above, preferably 150° C. or above, and possessing a functional group having radical reactivity at one terminal of the molecule, which are usable in this invention, are those represented by the following formula:

$$R^{10}-CO+X-Ar-CO)_{\overline{n}}OR^{20}$$

(wherein X is selected from O and S; Ar is a divalent arylene group; when $R^{10}$ is a functional group having radical reactivity, $R^{20}$ is selected from hydrogen, alkyl group of 1–10 carbon atoms and aryl group of 6–20 carbon atoms, and when $R^{20}$ is a functional group having radical reactivity, $R^{10}$ is selected from alkyl group of 1–10 carbon atoms and aryl group of 6–20 carbon atoms; and n is 2–10 on a number average).

As a functional group having radical reactivity, there can be mentioned a group having an arylmaleimide structure, preferably the one of the formula:

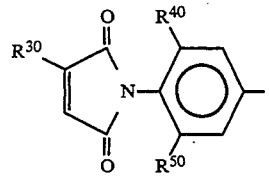

(wherein $R^{30}$, $R^{40}$ and $R^{50}$ are each selected from hydrogen and alkyl group of 1–4 carbon atoms).

Said aromatic oligomers can be produced from a polycondensation reaction using carboxyarylmaleimide or hydroxyarylmaleimide and hydroxyarylcarboxylic acid as starting materials. Preferably, said materials are polycondensed by acetylating the hydroxyl groups with an acetylating agent such as acetic anhydride or acetyl chloride and then distilling away acetic acid. This process can be applied when X is S.

The aromatic oligomers used in this invention, namely the aromatic oligomers having a functional group with radical reactivity at one terminal of the molecule can be reacted as a grafting agent with various kinds of polymeric materials having radical reactivity to realize enhancement of performance and functional capability of said polymeric materials.

Especially, by reacting such an oligomer with a thermoplastic polymeric material having a glass transition temperature of 10° C. or below to synthesize a graft copolymer, it is possible to produce a thermoplastic elastomer having high thermal resistance.

The method for the above reaction is not specifically defined, but the reaction effectuated by melt mixing is preferred. For promoting grafting, a radical initiator effective at said reaction temperature may be properly selected. As such a radical initiator, tertiary-butyl hydroperoxide, cumyl hydroperoxide and the like can be mentioned.

As the method for preparing a thermoplastic graft copolymer of this invention, there can be mentioned a method in which a polymer having a glass transition temperature of 10° C. or below and possessing unsaturated double bonds in its structure is reacted with an aromatic oligomer having a flow temperature of 100° C. or above and possessing, at one terminal of the molecule, a functional group reactable with the unsaturated double bonds.

As the polymers having a glass transition temperature of 10° C. or below and possessing unsaturated double bonds in its structure, which are usable in this invention, there can be mentioned, for example, ethylene-propylene-butadiene terpolymer, ethylene-propylene-isoprene terpolymer, ethylene-propylene-1,5-hexadiene terpolymer, ethylene-propylene-dicyclopentadiene terpolymer and ethylene-propylene-ethylidenenorbornene terpolymer.

The aromatic oligomers having a flow temperature of 100° C. or above, preferably 150° C. or above, and possessing, at one terminal of the molecule, a functional group reactable with the unsaturated double bonds, which are usable in this invention, are preferably those represented by the following formula:

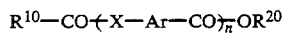

$$R^{10}-CO+X-Ar-CO)_{\overline{n}}OR^{20}$$

(wherein X is selected from O and S; Ar is a divalent arylene group; when $R^{10}$ is a functional group having radical reactivity, $R^{20}$ is selected from hydrogen, alkyl group of 1-10 carbon atoms and aryl group of 6-20 carbon atoms, and when $R^{20}$ is a functional group having radical reactivity, $R^{10}$ is selected from alkyl group of 1-10 carbon atoms and aryl group of 6-20 carbon atoms; and n is 2-10 on a number average).

Preferred examples of the groups having a functional group reactable with unsaturated double bonds are halomethylaryl group and tertiary haloalkyl group. Halomethylaryl group is especially preferred.

Said aromatic oligomers can be produced from a polycondensation reaction using halomethylarylcarboxylic acid and acetoxyarylcarboxylic acid as starting materials. Preferably, polycondensation is effectuated by acetylating the hydroxyl group with an acetylating agent such as acetic anhydride or acetyl chloride and then distilling away acetic acid. The same procedure can be applied when X is S.

The aromatic oligomers used in this invention, namely the aromatic oligomers having at one terminal of the molecule a functional group reactable with unsaturated double bonds can be reacted as a grafting agent with various kinds of polymeric materials containing unsaturated double bonds in the structure to realize enhancement of performance and functional capability of said polymeric materials.

Especially, by reacting said aromatic oligomer with a thermoplastic polymeric material having unsaturated double bonds and a glass transition temperature of 10° C. or below to synthesize a graft copolymer, it is possible to produce a thermoplastic elastomer having high thermal resistance.

Further, a detailed description will be given below on the case where the main chain of the thermoplastic graft copolymer is an organopolysiloxane.

As combinations of reactive functional group in the main chain organopolysiloxane and reactable functional group in the side chain, there can be mentioned the combinations of amino group-containing organic group bonded to silicon and acid anhydride group, epoxy group-containing organic group bonded to silicon and carboxyl group, and hydrogen atom bonded to silicon and unsaturated double bond.

The modified organopolysiloxanes usable in this invention are those represented by the following formula (IV):

(wherein $R^1$, $R^2$ and $R^3$ are each selected from hydrocarbons of 1-4 carbon atoms and

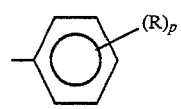

wherein R is a hydrocarbon of 1-3 carbon atoms and p is a number of 0-2; $R^4$ is hydrogen or a group selected from —$X_1$—R', —$X_2$—NH—$X_3$—R' and —$X_2$—O—$X_3$—R' wherein R' is selected from amino group and epoxy group, $X_1$ is a hydrocarbon of 1-20 carbon atoms, and $X_2$ and $X_3$ are each a hydrocarbon of 1-10 carbon atoms; and m and n are each a number so selected that the equivalent of said functional group will be about 500-10,000, preferably about 2,000-4,000).

Among these organopolysiloxanes, preferred are those of the formula (IV) wherein $R^1$, $R^2$ and $R^3$ are each selected from $CH_3$, —$C_2H_5$ and

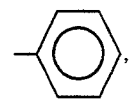

and $R^4$ is selected from

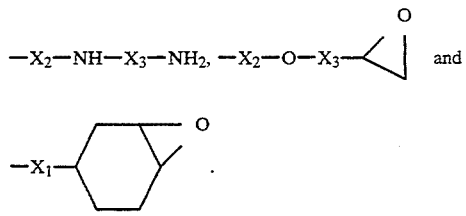

Next, in case the main chain is an organopolysiloxane, the aromatic oligomer of this invention in the side chain is represented by the following formula (V):

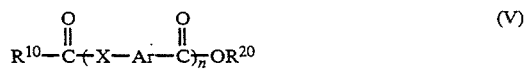

(wherein X is selected from O and S, and Ar is a divalent arylene group).

Here, in case the main chain organopolysiloxane has an epoxy group as reactive functional group, the aromatic oligomer in the side chain is preferably the one which has a carboxyl group at one terminal of the molecule.

That is, in the formula (V), $R^{20}$ is preferably hydrogen, the formula (V) preferably coincides with the afore-shown formula (II), and also $R^{10}$, Ar and n are preferably the same as those in the formula (II).

In case the main chain organopolysiloxane has an amino group as reactive functional group, the aromatic oligomer of this invention in the side chain is preferably the one which has an acid anhydride group at one terminal of the molecule.

That is, the formula (V) preferably coincides with the afore-shown formula (III), and also $R^{10}$, $R^{20}$, Ar and n are preferably the same as those in the formula (III).

Further, in case the main chain organopolysiloxaae has hydrogen atom bonded to silicon as reactive functional group, the aromatic oligomer in the side chain is the one which has an unsaturated double bond at one terminal of the molecule.

That is, the formula (V) coincides with the aforeshown formula (III), and further, $R^{10}$ or $R^{20}$ is an organic group of 3–20 carbon atoms which has an unsaturated double bond(s) and may contain a hetero atom. When $R^{10}$ is an organic group containing an unsaturated double bond(s), $R^{20}$ is a group inert to the reaction, and when $R^{20}$ is an organic group containing an unsaturated double bond(s), $R^{10}$ is a group inert to the reaction.

For promoting grafting, it is recommended to add platinum or a platinum compound in case the functional group in said polysiloxane is hydrogen atom bonded to silicon and the functional group in the aromatic polymer selected is unsaturated double bond, and to add a phosphinic catalyst, a tertiary amine or the like in the case of combination of epoxy group and carboxyl group. Also, an ordinary organic solvent such as 1-methyl-2-pyrrolidone may be used if necessary.

The means for blending the oligomer in a polymeric material is not specified in this invention. That is, generally, a polymeric material and said oligomer, after mixed as desired with a pigment, heat stabilizer, reaction catalyst, etc., by a Henschel mixer, tumbler, etc., are subjected to melt mixing by an extruder, Banbury mixer or other means.

Further, the oligomers of this invention may be added as desired with a filler or fillers generally used for the polymeric materials. That is, said oligomers may be added with a fibrous reinforcing agent such as glass fiber, silica-alumina fiber, alumina fiber, wollastonite, carbon fiber, potassium titanate fiber, etc., an inorganic filler such as calcium carbonate, clay, mica, glass beads, etc., a solid lubricant such as polytetrafluoroethylene, graphite, etc., antioxidant, heat stabilizer and other additives.

The following facts may be pointed out as the reasons why the melt liquid crystalline oligomers of this invention can act very effectively as a modifier for polymeric materials.

Firstly, the degree of polymerization of said oligomers is low enough to cause melting of the oligomers at the time of mixing, and said oligomers can be mixed well or react with polymeric materials. Also, when said oligomers are rendered into a liquid crystalline state when melted, the molecular chain is linear and very rigid.

Therefore, the end energy of the oligomer itself is very high, and in case the polymeric material added with said oligomer is crystalline, the oligomer induces formation of crystal nucleus to enable realization of enhancement of strength and thermal resistance of said polymeric material.

Also, in case said oligomer is grafted to an appropriate flexible polymeric material, the oligomer-rich region in said material matrix serves as the solid physical crosslinking point, enabling development of a thermoplastic elastomer with excellent thermal resistance. Thus, use of the oligomers of this invention makes it possible to realize the excellent functions that could never be obtained with use of the conventional oligomers.

These presumptions, however, are in no way restrictive to the present invention.

It is made possible to provide a polymeric material with unprecedentedly high performance by making use of rigidity and low-molecular weight characteristic of aromatic oligomers.

The aromatic oligomers of this invention are melted at high temperatures, and it is possible to produce a thermoplastic elastomer by graft copolymerizing said oligomer by reacting it with a polymer which is low in glass transition temperature ($Tg \leq 10°$ C.) and has a functional group reactable with the aromatic oligomers, so that the oligomers of this invention are very useful.

Also, the elastomer obtained according to this method shows the behavior as an excellent rubber-like elastic material in the wide temperature range from room temperature to a very high temperature, so that such an elastomer finds a very wide scope of use, for example as material for various kinds of hoses such as oil cooler hose, air duct hose, power stearing hose, control hose, oil return hose, heat-resisting hose, etc., material for various types of seals such as oil seal, O-ring, packing, gasket, etc., and material for various types of diaphragm, rubber plate, belt, oil level gage, hose masking, sound insulator, etc.

Further, the aromatic oligomers of this invention are capable, with addition of a small quantity thereof, of improving fluidity of the polyesters showing liquid crystallinity in the melting state. They also have the effect of a nucleus forming agent for the crystalline resins such as polypropylene, polyethylene terephthalate, polyphenylene sulfide, etc.

Best Mode for Carrying out the Invention

The embodiments of the present invention are shown below. It is to be understood, however, that these embodiments are in no way restrictive to the scope of the invention. The physical properties shown in the Examples were determined by the following methods. Gel permeation chromatography (hereinafter referred to as GPC):

Conducted with HLC-8020 mfd. by Tosoh Co., Ltd., by using a mixed solution of 2,3,5,6-tetrafluorophenol (TFP) and chloroform (TFP/CHCl$_3$=1/2.721 by volume) as mobile phase. Column: 7.8 mm in inner diameter and 30 cm in length. 5 mg of test sample was dissolved in 5 ml of 2,3,5,6-tetrafluorophenol, and this solution was diluted twice by volume with chloroform and then prefiltered with a 0.45 μm pore-size filter to measure the number-average degree of polymerization.

High-performance Liquid Chromatography
(hereinafter referred to as HPLC)

Measurement was made according to low-pressure gradient method by using a Multi-Solvent Liquid Feed System 600E mfd. by Waters Co., Ltd. and using methanol/acetic acid (1,000/5 by volume) and water/acetic acid (1,000/5 by volume) as mobile phase. Column: octadecyl silyl (ODS) column measuring 6.0 mm in inner diameter and 15 cm in length. Quantitative calculations were made according to the absolute calibration method.

Flow Temperature

This is the temperature at which the molten oligomer shows a melt viscosity of 48,000 poises when the molten oligomer heated at a rate of 4° C./min is extruded from a nozzle of 1 mm in inner diameter and 10 mm in length under a load of 100 kg/cm$^2$. Measured by a flow tester CFT-500 mfd. by Shimazdu Corporation. This flow temperature serves as a simple measure of the polymerization degree.

Optical Anisotropy

Optical anisotropy of the resin in a melted state was judged by microscopical observation of a powdery oligomer placed on a heating stage and heated at a rate of 10° C./min under polarized light. In case the oligomer was not perfectly melted under a stationary state, determination was made under pressure by making use of spring pressure.

Tensile Test

Measurements were made according to ASTM D-638 by using a tensile tester Tensilon EM-500 mfd. by Toyo Baldwin Co., Ltd. As regards permanent set, in case elongation at break exceeded 600%, the test piece was kept as it was for 10 minutes after 300% elongation and then contracted, and elongation 10 minutes thereafter was measured.

Compression Set Test

Compression set was determined according to JIS K-6301 by using a constant strain compression tester mfd. by Toyo Seiki Seisaku-sho Ltd.

Shore Hardness

Measured according to ASTM D-2240 by using a Shore hardness tester mfd. by Toyo Seiki Seisaku-sho Ltd. Sample thickness was 4.2 mm. Measurement was made at intervals of 15 seconds.

Melt Index

Determined by a melt indexer mfd. by Toyo Seiki Seisaku-sho Ltd. (The determination conditions are shown in the tables.)

EXAMPLES 1-8 AND COMPARATIVE EXAMPLE 1

(Synthesis of melt liquid crystalline oligomers having a carboxyl group at one terminal of the molecule and a hydroxyl group at the other terminal according to the acetylation method)

The syntheses of the oligomers composed of the POB structural units of n-mers (n is di, tri, tetra, penta, hexa, hepta, octa, nona or dodeca) alone were carried out according to the following procedure. The cases where n is di, tri, tetra, penta, hexa, hepta, octa or nona are represented by Examples 1, 2, 3, 4, 5, 6, 7 and 8, respectively, and the case where n is dodeca is represented by Comparative example 1.

10 mols of parahydroxybenzoic acid and 10(n−1)/n mols of acetic anhydride were supplied into a polymerizer provided with an anchor shaped agitator and having its interior atmosphere replaced sufficiently with nitrogen, and the mixture was heated with stirring under a nitrogen gas atmosphere. As the temperature reached 180° C., the mixture was reacted under reflux for 3 hours to effectuate acetylation. Thereafter, the temperature was raised to 300° C. and the reaction was continued until effusion of acetic acid generated as by-product of acetylation and that generated as by-product of condensation ceased. The reaction system was gradually cooled while crushing the reaction product under strong stirring, and after the temperature dropped to less than 120° C., the reaction mixture was taken out of the system. This reaction mixture was ground into the particles of less than 200 μm by a bantam mill manufactured by Hosokawa Micron Co., Ltd.

Assuming that there has been achieved 100% acetylation, the number-average degree of polymerization of the oligomers corresponding to the n-mers (n being di, tri, tetra, penta, hexa, hepta, octa, nona or dodeca) as calculated from the amount of by-product acetic acid effused were 1.8, 2.6, 3.5, 4.3, 5.3, 6.2, 7.1, 8.0 and 10.6, while the number-average degree of polymerization of the oligomers corresponding to di- to nonamer as determined by the GPC method were 1.82, 2.69, 3.52, 4.36, 5.32, 6.26, 7.18 and 8.55, respectively. Further, the weight fractions of the monomer and dimer present in these oligomers were 46.9%, 24.0%, 19.2%, 13.1%, 11.9%, 9.7%, 9.2% and 8.1%, respectively. Also, the flow temperatures of these oligomers and the temperatures exhibiting optical anisotropy were determined by the above-described methods. The oligomers whose number-average degree of polymerization as calculated from effluence of acetic acid was 8.0 or less showed melt liquid crystallinity, but the oligomer with a number-average degree of polymerization of 10.6 showed no fluidity even when heated to 500° C. nor it showed optical anisotropy even under pressure. These and other results obtained are shown collectively in Table 1.

Further, in order to confirm the terminal group of these oligomers, their infrared absorption spectra were measured according to the KBr method. As a result, a peak due to hydroxyl group was detected at around 3,500 cm$^{-1}$ for each oligomer, but there was detected no peak due to acetyl group at 1,370 m$^{-1}$. This indicates that each of the oligomers is terminated with parahydroxybenzoic acid which has not undergone acetylation.

EXAMPLE 9

(Methanol-washed oligomer having a carboxyl group at one terminal of the molecule and a hydroxyl group at the other terminal)

500 ml of methanol was added to 50 g of an oligomer corresponding to the pentamer obtained in Example 4, and the mixture was stirred under methanol refluxing for 30 minutes and filtered while maintaining the temperature at 60° C. The cakes were recovered and dried to obtain 42.5 g of a methanol-washed oligomer.

The results of determinations of weight fraction of monomer and dimer in the obtained oligomer, its number-average degree of polymerization, its flow temperature and temperature at which it shows optical anisotropy are shown in Table 2 (Example 9).

It was also confirmed that in case said oligomer was washed with distilled water, almost all of the dimer and monomer remained present, while in case said oligomer was washed with pyridine, the hexamer to dimer were lost.

Further, weight loss on heating to 400° C. was measured for the oligomer before methanol washing (Example 4) and the oligomer after methanol washing (Example 9). The weight loss was 18.3% for the former and 13.3% for the latter. It was found that thermal stability was improved as almost all of the dimer and monomer were removed by methanol washing.

EXAMPLE 10

(Methanol-washed oligomer having a carboxyl group at one terminal of the molecule and a maleimide at the other terminal)

0.4 mol (86.8 g) of N-(4-carboxyphenyl)maleimide, 0.8 mol of (110.4 g) of p-hydroxybenzoic acid and 0.88 mol (90 g) of acetic anhydride were supplied into a 500 ml separable flask equipped with an anchor shaped agitator, a three-way stop cock and a Dimroth condenser. A Teflon sheet cut to an appropriate size was used as packing disposed between the upper and lower portions of said flask. The anchor shaped agitator was turned at 120 r.p.m., nitrogen was introduced into the flask through the three-way stop cock to place the system under a nitrogen atmosphere and cooling water was passed into the Dimroth condenser. Under this state, the separable flask was placed in an oil bath and the latter was heated to 160° C. With the oil bath kept at 160° C., the mixture in the flask was subjected to an acetylation reaction for 3 hours under reflux of acetic anhydride. Upon the end of the acetylation reaction, the Dimroth condenser was quickly replaced with a Liebig condenser and the oil bath was further heated to 240° C. The oil bath was maintained at 240° C. and acetic acid and acetic anhydride released out of the system were recovered from the Liebig condenser. Recovery of acetic acid, etc., was conducted after exchange of the Dimroth condenser with a Liebig condenser, and the polycondensation was terminated at the point when 95.28 g of acetic acid, etc., was recovered in about 1.5 hours.

After the completion of the polycondensation, the oligomer was taken out and pulverized by a pulverizer. This oligomer power was washed with methanol in the same way as described above.

The results of determinations of weight fraction of monomer and dimer in the obtained oligomer, its number-average degree of polymerization in the structural formula shown below, its flow temperature and temperature at which said oligomer showed optical anisotropy are shown in Table 2.

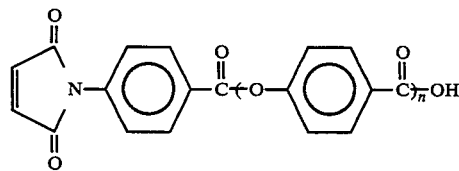

EXAMPLE 11

(Methanol-washed oligomer having a methyl ester at one terminal of the molecule and a hydroxyl group at the other terminal)

0.2 mol (30.43 g) of methyl p-hydroxybenzoate, 1.0 mol (206.32 g) of N,N'-dicyclohexylcarbodiimide and about 10 g of a pyridine salt of p-toluenesulfonic acid were dissolved in 800 ml of pyridine. Separately, 0.83 mol (115.1 g) of p-hydroxybenzoic acid was dissolved in 800 ml of pyridine, and these two solutions were mixed at room temperature. When the mixed solution was stirred at room temperature, the reaction solution became cloudy in about 5 minutes. After 8-hour stirring of the solution, the precipitated oligomer and N,N'-dicyclohexylurea were filtered out and recovered. The recovered material was washed well with methanol by using a Soxhlet extractor and dried. There was obtained 151.93 g of an oligomer.

The results of determinations of weight fraction of monomer and dimer in the obtained oligomer, its number-average polymerization degree in the structural formula shown below, its flow temperature and temperature at which said oligomer showed optical anisotropy are shown in Table 2.

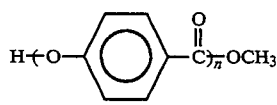

EXAMPLE 12

(Modification of hydroxyl terminal)

185.4 g of the oligomer obtained in Example 9, 0.33 mol (33.66 g) of acetic anhydride, 1 ml of pyridine, 0.5 g of potassium acetate and 200 ml of dibenzyltoluene were supplied into a polymerizer similar to that used in Example 10, and with the oil bath kept at 160° C., the mixture was subjected to a 3-hour acetylation reaction under reflux of acetic anhydride. Thereafter, the reaction product was washed twice with acetone and twice with methanol, and the washed oligomer was dried. In order to confirm that the hydroxyl terminal of this oligomer had been acetylated, the IR absorption spectrum of said oligomer was measured according to the KBr method. As a result, it was found that the peak due to the hydroxyl group at around 3,500 cm$^{-1}$ disappeared, and an absorption at around 1,370 cm$^{-1}$ due to the acetyl group was confirmed. This ascertained acetylation of the hydroxyl terminal of the oligomer.

The results of determinations of weight fraction of monomer and dimer in the obtained oligomer, its number-average degree of polymerization, its flow temperature and temperature at which it showed optical anisotropy are shown in Table 2.

APPLICATION EXAMPLE 1 AND COMPARATIVE APPLICATION EXAMPLE 1

(Example of utilization of melt liquid crystalline oligomer: fluidity improver for melt liquid crystalline polyester)

A melt liquid crystalline polyester composed of the following recurring structural units was synthesized according to an acetylation method.

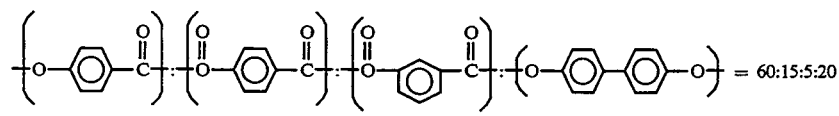

The obtained polyester had a flow temperature of 324° C. and showed melt liquid crystallinity at temperatures 340° C. or above. 100 parts by weight of this melt liquid crystalline polyester, 67 parts by weight of glass fiber (EFH 75-01 produced by Central Glass Co., Ltd.) and 3 parts by weight of the oligomer obtained in Example 1 were mixed by a Henschel mixer and the mixture was melted and kneaded at 320°–330° C. and made into pellets by using a twin-screw extruder (PCM-30 mfd. by Ikegai Iron Works Co., Ltd.) (Application Example 1). There were likewise obtained the pellets, at a temperature of 330° C., from a composition comprising said melt liquid crystalline polyester and glass fiber and not containing said oligomer (Comparative Application Example 1).

The thin-wall fluidity of the composition was measured by injection molding from the obtained pellets. The "thin-wall fluidity" is a property which indicates the degree of moldability and is determined in the manner described below.

Thin-wall fluidity: The composition of this invention was charged in a molten state, under the given injecting conditions, into a mold having four separate rectangular cavities measuring 0.3 mm in wall thickness, 46 mm in length and 5 mm in width, and the flow length in the longitudinal direction in each of the four rectangles was measured. The average of the four measurements was given as flow length. Cylinder temperature: 340° C. and 360° C.; mold temperature: 130° C.

Further, bending strength, bending modulus (measured according to ASTM D-790), unnotched Izod impact strength (measured according to ASTM D-256) and thermal deformation temperature (measured according to ASTM D-648) were measured. The results are shown in Table 3.

It is apparent from Table 3 that the composition of Application Example 1 in which the melt liquid crystalline oligomer of this invention is incorporated is remarkably improved in fluidity while maintaining substantially unaffected the mechanical properties and heat resistance of the composition of Comparative Application Example 1 in which no said oligomer is used.

APPLICATION EXAMPLES 2 AND 3 AND COMPARATIVE APPLICATION EXAMPLES 2 AND 3

(Example of utilization of melt liquid crystalline oligomer: crystalline property and fluidity improver for crystalline polyester)

A polyethylene terephthalate resin having a solution viscosity (measured by Ubbelohdea's viscometer at 20° C. using phenol/tetrachloroethane (6/4 by volume) as solvent) of 0.55 dl/g was synthesized according to a conventional method. Then, 5 parts by weight of the oligomer described in Example 9 was added to 100 parts by weight of said polyethylene terephthalate resin and the mixture was dried in vacuo at 130° C. for 5 hours, after which 0.1 part by weight of triphenyl phosphate was further added and total 40 g of the mixture was melted and kneaded by using Laboplastomill mfd. by Toyo Seiki Seisaku-sho Ltd. at 290° C. and 50 r.p.m. under a high-purity nitrogen atmosphere for 10 minutes (Application Example 2).

There was also prepared a similarly melted and kneaded product of said polyethylene terephthalate resin containing no said oligomer (Comparative Application Example 2).

10 mg of each of these compositions was heated and melted at 330° C. for 5 minutes and the peak of heat generation concomitant with crystallization was measured by a differential scanning calorimeter (DSC) at a temperature reducing rate of 10°/min. The peak temperature was determined as the crystallization temperature. In the case of Comparative Application Example 2, the crystallization temperature was 190.2° C. whereas that of the composition prepared in Application Example 2 was 206.3° C. This demonstrates that said oligomer has a crystal nucleus forming action for the polyethylene terephthalate resin.

Further, 100 parts by weight of this polyethylene terephthalate resin, 67 parts by weight of glass fiber (EFH 75-01 produced by Central Glass Co., Ltd.) and 5 parts by weight of the oligomer described in Example 9 were mixed by a Henschel mixer and the mixture was melted and kneaded at 265° C. similarly to Application Example 1 to obtain the pellets (Application Example 3). There were likewise obtained the pellets from the composition comprising said melt liquid crystalline polyester and glass fiber and not containing said oligomer (Comparative Application Example 3).

The thin-wall fluidity of said compositions was measured in the same way as Application Example 1 by molding said pellets at a cylinder temperature of 270° C. and a mold temperature of 75° C. In the case of composition of Comparative Application Example 3, the thin-wall flow length was 6.2 mm while that of the composition of Application Example 3 was 10.2 mm.

These results indicate that said oligomer has not only a crystal nucleus forming action but also a fluidity improving effect.

EXAMPLE 13

An aromatic oligomer having a carboxyl group at one end of the molecule was synthesized in the manner described below. 0.4 mol (48.8 g) of benzoic acid, 0.8 mol (110.4 g) of p-hydroxybenzoic acid and 0.88 mol (90 g) of acetic anhydride were fed into a 500 ml separable flask furnished with an anchor shaped agitator, a three-way stop cock and a Dimroth condenser. A properly sized Teflon sheet was used as packing between the upper and lower portions of the flask. The anchor shaped agitator was turned at 120 r.p.m., nitrogen was introduced through the three-way stop cock to place the system under a nitrogen atmosphere and cooling water was passed into the Dimroth condenser. In this state, the separable flask was placed in an oil bath and the latter was heated to 160° C. With the oil bath kept at 160° C., the mixture in the flask was subjected to a 2-hour acetylation reaction under reflux of acetic anhydride. Upon completion of the acetylation reaction, the Dimroth condenser was quickly replaced with a Liebig condenser and the oil bath was further heated to 260° C. About 40 minutes were required for raising the oil bath temperature from 160° C. to 260° C. Thereafter, the oil bath temperature was kept at 260° C. and the acetic acid and acetic anhydride exuding from the system were recovered by the Liebig condenser. Recovery of acetic acid, etc., was conducted after replacement of the Dimroth condenser with a Liebig condenser. The polycondensation was terminated at the point when 104 g of acetic acid, etc., was recovered in about one hour.

After the end of polycondensation, the oligomer was taken out and pulverized by a pulverizer. There was obtained 130 g of powder. This powder was washed with 10 times as much amount (1,300 g) of methanol in the manner described below to remove the low-molecular weight matter soluble in methanol. 130 g of said powder and 1,300 g of methanol were supplied into a 2-liter separable flask. The flask was adapted with an anchor shaped agitator and a Dimroth condenser and placed in an oil bath of 80° C. such that methanol could be refluxed in the system, and the mixture in the flask was washed under methanol refluxing for one hour. Upon completion of washing, the mixture was immediately filtered and the oligomer was recovered. Further, this recovered oligomer was dried in a vacuum drier at 80° C. for 10 hours to obtain an aromatic oligomer having a carboxyl group alone at one end of the molecule. There was obtained 85.8 g of the oligomer in a yield of 66%.

The flow temperature of the purified oligomer was measured. It was 182° C. Then, the weight loss on heating of this purified oligomer was measured by using the previously mentioned apparatus TGA-50 at a heating rate of 10° C./min under a nitrogen atmosphere. As a result, it was found that this purified oligomer was stable up to a temperature close to 300° C. The temperature at which this purified oligomer showed optimal anisotropy was 202° C.

Shown below is the result of measurement of molecular weight distribution of said purified oligomer. Measurement was made by using HLC-8020 with column size of 7.8 mm ID×30 cm, manufactured by Tosoh Co., Ltd. The test sample was prepared by dissolving 5 mg of said oligomer in 5 ml of tetrafluorophenol, diluting the resulting solution twice by volume with chloroform and prefiltering the diluted solution with a 0.45 μm filter. A mixed solution of tetrafluorophenol and chloroform (tetrafluorophenol/chloroform=1/2.721 by volume) was used as mobile phase. As a result of fractionation according to a conventional method and mass spectrometric analysis, it was found that the peak at retention time of 54.48 minutes was n=1 in the following formula. It was also learned that the peaks at 52.57 minutes, 51.35 minutes, 50.47 minutes and 49.85 minutes corresponded to n=2, 3, 4 and 5, respectively.

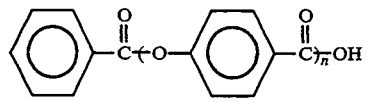

From this measurement, the number-average degree of polymerization of said oligomer was given as n=3.5 in the above formula. Also, the Q value (weight-average molecular weight/number-average molecular weight) of said polymer was about 1.55.

In the above measurement of molecular weight distribution, since the high-molecular weight component of said oligomer is not dissolved in tetrafluorophenol, the molecular weight distribution of only the portion dissolved in filtered tetrafluorophenol is measured.

For measuring the number-average molecular weight of said aromatic oligomer more exactly, the number-average molecular weight was determined according to a chemical decomposition method described below. The "chemical decomposition method" referred to herein is a method according to which said aromatic oligomer is decomposed into monomer units in N-methylpyrrolidone, using n-butylamine as decomposing agent, by chemically severing the ester linkage of said oligomer, and the decomposed components are identified and quantified by liquid chromatography, determining the number-average degree of polymerization from the number of the terminal groups.

More specifically, 50 mg of said oligomer was supplied into an egg plant type flask containing 40 ml of N-methylpyrrolidone and 10 ml of n-butylamine, and subjected to 12-hour decomposition under stirring with a magnetic stirrer in an 80° C. oil bath provided with a condenser, thus decomposing said oligomer into N-n-butylbenzamide, N-n-butyl-p-hydroxybenzamide and p-hydroxybenzoic acid, and after removing excess n-butylamine by an evaporator, the residue was filtered with a membrane filter with a pore size of 0.45 microns, the resulting product being used as test sample.

Measurement was made by using a high-performance liquid chromatographic system mfd. by Tosoh Co., Ltd. (pump: TOSOH CCPM, pump controller: TOSOH PX-8010, gradienter: TOSOH GE-8000, dynamic mixer: TOSOH MX-8010, UV detector: TOSOH MX-8010 (used at detecting wavelength of 254 nm), recorder: Chromato-Recorder 12 mfd. by System Instruments Co., Ltd, column: TOSOH TSK-Gel ODS-120T), and each component was eluted and quantified according to a water-methanol gradient elution method.

The water used as solvent was a 1000/5 (by volume) mixture of ion exchange water and acetic acid, and the methanol used was a 1000/5 (by volume) mixture of electronic industrial grade methanol produced by Sumitomo Chemical Industries Co., Ltd. and acetic acid. As for the gradient conditions, measurement was made at the aqueous system concentrations of 75 vol % for 0 minute, 60 vol % for 30 minutes, 0 vol % for 50 minutes and 75 vol % for 60 minutes (in each case the concentration was changed linearly).

The results of quantification, conducted under the above-said conditions, of the respective components contained in said sample showed that p-hydroxybenzoic acid/N-n-butyl -p-hydroxybenzamide/N-n-butylbenzamide=1.0/3.2/1.0 (in molar ratio), and the number-average degree of polymerization of said oligomer was n=4.2 in the above-shown formula.

APPLICATION EXAMPLE 4

An ethylene-methyl acrylate-glycidyl methacrylate terpolymer (ethylene: methyl acrylate: glycidyl methacrylate=35:63:2 (by weight ratio); MI=8.7 g/10 min (at 190° C. under a load of 2.16 kg)) was obtained according to the method shown in Japanese Patent Application Kokai No. 61-127709, Example 5. The glass transition temperature of this polymer was measured by a stand-alone type differential scanning calorimeter Model DSC-50 mfd. by Shimadzu Corp., in a nitrogen atmosphere at a heating rate of 10° C./min. From the obtained chart, the endotherm starting temperature was determined by the tangential method according to the conventional principle, and the thus determined temperature was given as glass transition temperature. It was −33.7° C. Also, weight loss on heating of said polymer was measured by a stand-alone type thermogravimeter TGA-50 (Shimadzu Corp.) in a nitrogen atmosphere at a heating rate of 10° C./min. The measurement showed that this polymer was thermally stable up to a temperature close to 350° C.

Then, the ethylene-methyl acrylate-glycidyl methacrylate terpolymer and an aromatic oligomer having a carboxyl group at one terminal of the molecule and represented by the formula shown in Example 13, with the number-average polymerization degree n determined according to GPC being 3.5 (n determined by the chemical decomposition method being 4.2), were melt kneaded and reacted together with triphenylphosphine at a weight ratio of ethylene-methyl acrylate-glycidyl methacrylate terpolymer/aromatic oligomer/triphenylphosphine=90/10/0.1 (=45 g/5 g/50 mg) by using Laboplastomill ME-15 mfd. by Toyo Seiki Seisaku-sho Ltd., equipped with a R-60 mixer and roller type blades, in a nitrogen atmosphere at 280° C. and 120 r.p.m. for 15 minutes to obtain a graft copolymer. MI of the thus obtained graft copolymer at 230° C. under a load of 10 kg was 4.5 g/10 min.

The graft efficiency of the obtained graft copolymer was calculated by the following analytical method. 500 mg of the obtained graft copolymer was subjected to previously described chemical decomposition in 40 ml of N-methylpyrrolidone and 10 ml of n-butylamine to decompose the aromatic oligomer portion. For removing the ethylene-methyl acrylate-glycidyl methacrylate copolymer, it was precipitated in 500 ml of methanol. After filtration, the filtrate was concentrated by an evaporator and, after removing methanol and excess n-butylamine, the residue was further filtered by a membrane filter with a pore size of 0.45 microns to prepare a test sample.

This sample was analyzed by high-performance liquid chromatography and the respective components were quantified by the same techniques as described above. Calculation can be made from the ratio of p-hydroxybenzoic acid amide to N-n-butylbenzamide which are decomposed from the aromatic oligomer moiety. More specifically, supposing that the ratio of p-hydroxybenzoic acid to N,n-butylbenzamide quantified as the decomposed components is x $$\left( = \frac{\text{p-hydroxybenzoic acid}}{\text{N-n-butylbenzamide}} \right),$$

the number-average degree of polymerization of the aromatic polymer used is n and the amount of the aromatic oligomer reacted is y (wt %), the graft efficiency can be calculated as follows:

$$G_1 = (1-x) \times 100 \ (\%)$$

wherein $G_1$ is the ratio of the aromatic oligomer reacted to the ethylene-methyl acrylate-glycidyl methacrylate terpolymer; and $$G_2 = \frac{(1-x) \times y \times 142}{(100-y) \times 0.02 \times (120n + 122)} \times 100 \ (\%)$$

wherein G2 is reaction efficiency of the epoxy group of the ethylene-methyl acrylate-glycidyl methacrylate terpolymer.

The thus determined graft efficiency is shown in Table 4.

This graft copolymer was worked into a 2.1 mm thick pressed sheet at 280° C. under a pressure of 50 kg/cm$^2$, and the test pieces for determining the various properties were cut out from this pressed sheet and subjected to determination of properties. The results are shown in Table 4.

APPLICATIONS EXAMPLES 5-7 AND COMPARATIVE APPLICATION EXAMPLE 4

The ethylene-methyl acrylate-glycidyl methacrylate terpolymer used in Application Example 4, the aromatic oligomer having a carboxyl group at one end of the molecule shown in Example 13 and triphenylphosphine were melt mixed at a composition ratio shown in Table 4, and reacted in the manner of Application Example 4 to obtain a graft copolymer, which was then worked into a pressed sheet and various properties were determined in the same way as Application Example 4. Similar determination of properties was made for the ethylene-methyl acrylate-glycidyl methacrylate terpolymer alone (Comparative Application Example 4). The results are shown in Table 4.

Also, graft efficiency was determined by the method shown in Application Example 4 for each of the graft copolymers obtained in Application Example Nos. 5-7. The results are shown in Table 4.

EXAMPLE 14

An oligomer having a carboxyl group at one terminal of the molecule was synthesized according to the method of Example 13. 0.4 mol of benzoic acid, 1.2 mol of p-hydroxybenzoic acid and 1.32 mol of acetic anhydride were supplied into a flask, and the mixture was acetylated and polycondensed.

The obtained oligomer was washed with methanol and dried in vacuo as in Example 13 to obtain a purified oligomer. The flow temperature of this purified oligomer was 202° C.

The number-average degree of polymerization of said oligomer as determined by the chemical decomposition method shown in Example 13 was n=4.8 in the formula shown previously. The Q value was 1.46. Said oligomer also showed optical anisotropy in the molten state.

APPLICATION EXAMPLE 8

The purified oligomer of Example 14, the ethylene-methyl acrylate-glycidyl methacrylate terpolymer used in application Example 4 and triphenylphosphine were melt mixed and reacted in the ratio (by weight) of ethylene-methyl acrylate-glycidyl methacrylate terpolymer/purified oligomer/triphenylphosphine =90/10/0.1 (=45 g/5 g/50 mg) under the same conditions as in Application Example 4 to obtain a graft copolymer. This graft copolymer was worked into a pressed sheet and the various properties were determined in the same way as Application Example 4. The results are shown in Table 4.

APPLICATION EXAMPLE 9

The ethylene-methyl acrylate-glycidyl methacrylate terpolymer used in Application Example 4, the aromatic oligomer having a carboxyl group at one terminal of the molecule obtained in Example 14 and triphenylphosphine were mixed at a ratio of 90 wt %/10 wt %/0.1 phr, and the mixture was kneaded and reacted five times repeatedly by using a 30 mm double-screw extruder PCM-30 of Ikegai Iron works Co., Ltd. at a cylinder temperature of 290° C., screw rotation speed of 200 r.p.m. and a feed rate of 3 kg/hr (residence time: about one minute) to obtain a graft copolymer.

A pressed sheet was made from this graft copolymer in the same way as Application Example 4 and its properties were determined in the same way as Application Example 4. The results are shown in Table 5.

Further, said graft copolymer was injection molded into a 35 mm×110 mm×2 mm flat sheet by using an injection molding machine IS-25EP-1A of Toshiba Machinery Co., Ltd. at a cylinder temperature of 280° C., and the test pieces for determining various properties were cut out from the sheet. The properties were determined in the same way as Application Example 4. The results are shown in Table 5.

EXAMPLE 15

An aromatic oligomer having a carboxyl group at one terminal of the molecule was synthesized by using the same method as Example 13. 0.3 mol of benzoic acid, 0.6 mol of p-hydroxybenzoic acid, 0.3 mol of meta-hydroxybenzoic acid and 1 mol of acetic anhydride were supplied, and the mixture was acetylated and polycondensed. The obtained oligomer was ground and then washed with methanol and dried in vacuo in the same way as Example 13 to obtain a purified oligomer.

The flow temperature of said purified oligomer was 141° C. The polymerization degree of the oligomer as determined by the chemical decomposition method described in Example 13 was n=7.6 in the formula shown below. The para-bond to meta-bond ratio (p/m) of the hydroxybenzoic acid unit was p/m=6.1/1.5. Also, said oligomer showed optical anisotropy in the molten state.

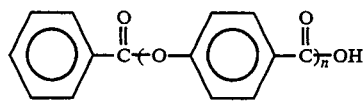

APPLICATION EXAMPLE 10

The purified oligomer obtained in example 15 and the ethylene-methyl acrylate-glycidyl methacrylate terpolymer used in Application Example 4 were melt mixed together with triphenylphosphine in a ratio (by weight) of ethylene-methyl acrylate-glycidyl methacrylate terpolymer/purified oligomer/triphenylphosphine= 86/14/0.1 (=43 g/7 g/50 mg) under the same conditions as Application Example 4 to obtain a graft copolymer. By using this graft copolymer, a pressed sheet was made and its properties were determined in the same way as Application Example 4. The results are shown in Table 5.

EXAMPLE 16

An aromatic oligomer synthesized by the method described below was prepared as the aromatic oligomer having a carboxyl group at one end of the molecule. Also, 4-mercaptobenzoic acid to be copolymerized with parahydroxybenzoic acid was synthesized according to the thiosalicylic acid synthesis method by C. F. H. Allen, D. D. Mckay et al (Org. Synth., 580 ff., 1943) and purified by sublimation.

Then, 0.1 mol (15.7 g) of 4-mercaptobenzoic acid, 0.1 mol (13.8 g) of p-hydroxybenzoic acid and 0.1 mol (12.2 g) of benzoic acid were dissolved in 300 ml of pyridine. Separately, 0.24 mol (49.44 g) of N,N'-dicyclohexylcarbodiimide and 2.5 g of p-toluenesulfonic acid were dissolved in 200 ml of pyridine, and these two solutions were mixed at room temperature.

As the mixed solution was stirred at room temperature, the reaction solution became cloudy in about 5 minutes. After 24-hour stirring of the solution, the precipitated aromatic oligomer and N,N'-dicyclohexylurea were filtered out and recovered. The recovered material was washed well with methanol and dried by using a Soxhlet extractor. There was obtained 21.1 g of aromatic oligomer.

Elemental analysis of the obtained aromatic oligomer showed C=65.5 wt %, H=3.6 wt %, S=9.5 wt % and O=21.1 wt %, and it was determined that the molecular structure of the oligomer was of the following formula:

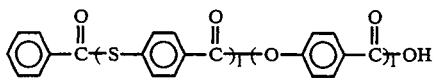

The flow temperature of said aromatic oligomer was 193.1° C. Further, as a result of measurement of weight loss on heating of this polymer by the method of Example 13, it was found that this polymer was stable up to a temperature close to 280° C. Also, said oligomer showed optical anisotropy in the molten state.

APPLICATION EXAMPLE 11

2.5 g of the aromatic oligomer obtained in Example 16, 2.5 g of the aromatic oligomer used in Example 13, 45 g of ethylene-methyl acrylate-glycidyl methacrylate terpolymer and 100 mg of triparatolylphosphine were melt mixed and reacted by using a mixer described in Example 13, at 270° C. and 120 r.p.m. for 5 minutes to obtain a graft copolymer.

By using this graft copolymer, a pressed sheet was prepared in the same way as Example 13, and a test piece for determining compression set was cut out from the sheet. The compression set of the sheet as determined under the conditions of 100° C. after 70 hours was 62.5%.

EXAMPLE 17

An aromatic oligomer having a carboxyl group at one end of the molecule was synthesized by using the same method as Example 16. First, 0.2 mol (31.4 g) of 4-mercaptobenzoic acid and 0.1 mol (12.2 g) of benzoic acid were dissolved in 300 ml of pyridine. Separately, 0.24 mol (49.44 g) of N,N'-dicyclohexylcarbodiimide and 2.5 g of p-toluenesulfonic acid were dissolved in 200 ml of pyridine, and these two solutions were mixed at room temperature.

After 24-hour stirring of the reaction solution, the precipitate was filtered out, washed with methanol and dried in the same way as Example 16 to obtain an aromatic oligomer. Elemental analysis of the obtained aromatic oligomer showed C=63.2 wt %, H=3.7 wt %, S=18.8 wt % and O=13.9 wt %, and it was determined that the molecular structure of the oligomer was of the following formula:

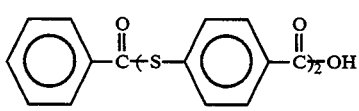

The flow temperature of said aromatic oligomer was 195.0° C. Also, said oligomer showed optical anisotropy in the molten state.

APPLICATION EXAMPLE 12

5 g of the aromatic oligomer obtained in Example 17, 45 g of the ethylene-methyl acrylate-glycidyl methacrylate terpolymer used in Application Example 4 and 50 mg of triparatolylphosphine were melt mixed and reacted by using a mixer described in Application Example 4, at 280° C. and 120 r.p.m. for 4 minutes to obtain a graft copolymer.

This graft copolymer was press molded into a sheet in the same way as Application Example 4 and the compression set of the sheet was determined (under the conditions of 70° C. after 22 hours). It was 39.8%.

EXAMPLE 18

An aromatic oligomer having an acid anhydride group at one terminal of the molecule was synthesized in the following way. 0.8 mol (110.4 g) of p-hydroxybenzoic acid and 0.88 mol (90 g) of acetic anhydride were supplied into a 500 ml separable flask equipped with an anchor shaped agitator, a three-way stop cock and a Dimroth condenser. A properly cut Teflon sheet was used as packing between the upper and lower portions of the flask. The anchor shaped agitator was turned at 120 r.p.m., nitrogen was introduced through the three-way stop cock to place the system under a nitrogen atmosphere and cooling water was passed into the Dimroth condenser. In this state, the separable flask was placed in an oil bath and the latter was heated to 160° C. With the oil bath kept at 160° C., the acetylation reaction was carried out while refluxing acetic anhydride for 2 hours. After completion of the acetylation reaction, the oil bath temperature was lowered for preventing evaporation of acetic acid and 0.4 mol (76.8 g) of trimellitic acid anhydride was added quickly. Also, the Dimroth condenser was quickly replaced with a Liebig condenser and the oil bath was heated to 260° C. Thereafter, the oil bath temperature was maintained at 260° C. and the acetic acid and acetic anhydride effusing out of the system were recovered by the Liebig condenser. Recovery of acetic acid, etc., was conducted after replacement of the Dimroth condenser with a Liebig condenser, and the polycondensation was terminated at a point when 98.2 g of acetic acid, etc., was recovered in about one hour.

After the end of polycondensation, the oligomer was taken out and pulverized by a pulverizer. There was obtained 142 g of powder. This powder was washed with 5 times as much amount (710 g) of dehydrated acetone in the manner described below and the low-molecular weight matter soluble in acetone was removed. 142 g of said powder and 710 g of dehydrated acetone were supplied into a 2-liter separable flask, and after setting an anchor shaped agitator and a Dimroth condenser to the separable flask, said flask was placed in an oil bath of 80° C. so that acetone could be refluxed in the system. Then washing was performed under acetone refluxing for one hour. After washing, the solution was immediately filtered and the oligomer was recovered. This recovered oligomer was dried by a vacuum dryer at 80° C. for 10 hours to obtain an aromatic oligomer having an acid anhydride group alone at one terminal of the molecule. There was obtained 98 g of oligomer in a yield of 69%.

The flow temperature of the obtained purified oligomer was 177° C. Then the weight loss on heating of this purified oligomer was measured by using a stand-alone thermogravimeter Model TGA-50 mfd. by Shimadzu Corp., in a nitrogen atmosphere at a heating rate of 10° C./min. As a result, it was found that said purified oligomer was stable up to a temperature close to 280° C.

In order to confirm that this purified oligomer is terminated at one end of its molecule with an acid anhydride derived from trimellitic acid anhydride, the infrared absorption spectrum of the oligomer was measured according to the KBr method. As a result, there was confirmed absorption due to acid anhydride at around 1783 cm$^{-1}$, which indicated that one end of the molecule of said oligomer was an acid anhydride.

Next, the method by which the number-average degree of polymerization of said purified oligomer was estimated is shown.

Aromatic oligomers were synthesized in a benzoic acid/parahydroxybenzoic acid ratio of $\frac{1}{2}$ to $\frac{1}{4}$ (by mole) according to the preparation process for a parahydroxybenzoic acid oligomer having a carboxyl group at one end of the molecule described in Example 13, and the flow temperature of the obtained oligomers was measured.

Further, each of the aromatic polymers was decomposed into N-n-butylbenzamide, N-n-butyl-p-hydroxybenzamide and p-hydroxybenzoic acid with n-butylamine in N-methylpyrrolidone, and the respective decomposed substances were quantified by high performance liquid chromatography according to a conventional method to determine the number-average molecular weight. As a result, it was found that there existed the following relation between the aromatic oligomer having a carboxyl group at one end of the molecule with a number-average degree of polymerization of n in the formula shown below and the flow temperature (FT(n)) of said aromatic oligomer:

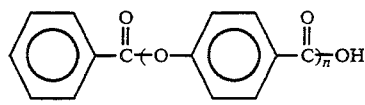

FT$_{(n)}$ (°C) = 32n + 50

The number-average degree of polymerization was estimated by applying this relationship to the synthesized reactive oligomer represented by the following formula:

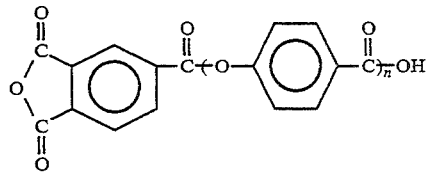

The result gave n=3.97.

Said oligomer also showed optical anisotropy in the molten state.

APPLICATION EXAMPLE 13

ESPRENE ® E-301A (ethylene: 46 wt %; propylene: 49 wt %, dicyclopentadiene: 5 wt %, iodine value: 10; produced by Sumitomo Chemical Industries Co., Ltd.) was used as ethylene-propylene-diene monomer terpolymer (hereinafter referred to as EPDM). 330 g of EPDM and 3,000 ml of toluene were supplied into a 5,000 ml separable flask equipped with a Teflon-made agitator, a 500 ml dropping funnel and a Dimroth condenser. A Teflon sheet cut to an appropriate shape and size was used as packing between the upper and lower portions of the flask. Cooling water was passed into the Dimroth condenser and the flask was placed in an oil bath of 100° C. to start heating to dissolve EPDM.

After EPDM has been perfectly dissolved, the separable flask was taken out of the oil bath and cooled to room temperature. Then a solution prepared by dissolving 0.15 mol (25 g) of metachloroperbenzoic acid in 500 ml of toluene was added dropwise from the dropping funnel over a period of one hour. After 12hour reaction at room temperature, the reaction solution was diluted till a moment before EPDM was precipitated with acetone (the amount of acetone required for this operation was about 500 ml). This reaction solution was poured into 30 liters of acetone with stirring, causing the polymer to precipitate. The obtained crude product was heated and re-dissolved in 3,000 ml of toluene and again precipitated in acetone to purify the polymer. The resultantly obtained epoxidated EPDM was air dried and then dried in vacuo. There was obtained 300 g of epoxidated EPDM in a yield of 90%.

The epoxy equivalent of said epoxidated EPDM was determined by back-titration. As a result, it was found that the epoxy equivalent of the obtained epoxidated EPDM was 5,000.

The epoxidated EPDM described above and the aromatic oligomer of Example 18 having a trimellitic acid anhydride group at one terminal of the molecule were mixed at a ratio of epoxidated EPDM to aromatic oligomer of 40 g to 10 g by Laboplastomill R-20 (mfd. by Toyo Seiki Seisaku-sho Ltd.) equipped with a R-60 mixer and roller type blades at 150° C. and 200 r.p.m. for one minute. The resulting mixture was further subjected to melt kneading by said Laboplastomill at 200° C. and 200 r.p.m. for 3 minutes to obtain a graft copolymer. The melt index of the thus obtained graft copolymer at 260° C. and under a load of 10 kg was 3.0 g/10 min.

This graft copolymer was worked into a 2.1 mm thick pressed sheet at 260° C. under a pressure of 50 kg/cm². A test piece for compression set was cut out from said sheet and its compression set was measured under the conditions of 70° C. after 22 hours. A tensile test piece and a Shore hardness test piece were also cut out from said sheet and 100% modulus, elongation at break, breaking strength, permanent set and Shore hardness of the test pieces were measured. The results are shown in Table 6.

EXAMPLE 19

An aromatic oligomer having a carboxyl group alone at one terminal of the molecule was obtained according to the process of Example 13 except for use of benzoic acid/p-hydroxybenzoic acid=0.4 mol/1.0 mol and 1.1 mol of acetic anhydride. The flow temperature of the purified oligomer after methanol washing was 195° C.

This oligomer showed optical anisotropy when melted.

APPLICATION EXAMPLE 14

150 g of EPDM (double bond: 0.06 equivalent) and 3,000 ml of hexane were supplied into a 5,000 ml separable flask furnished with Teflon-made agitating blades, a nitrogen conduit and a Dimroth condenser. Cooling water was passed into the Dimroth condenser and nitrogen was introduced into the flask from the nitrogen conduit at a flow rate of 30 ml/min, and in this state the flask was placed in an oil bath of 80° C. to start heating to dissolve EPDM. After EPDM has been perfectly dissolved, refluxing under heating was further continued for 2 hours to effectuate deaeration.

0.12 mol (17.2 g) of glycidyl methacrylate and 0.12 mol (15.2 g) of butyl acrylate were added to the mixture, followed by further addition of a solution prepared by dissolving 0.0032 mol (0.80 g) of azobis(2,4-dimethylvaleronitrile) in 20 ml of hexane. The mixture was reacted at the hexane refluxing temperature for 10 hours and then diluted with acetone till a moment before precipitation of EPDM. (The amount of acetone required for this operation was about 300 ml). The resulting solution was poured into 30 liters of acetone with stirring, causing sedimentation of the polymer. The obtained crude product was heated and redissolved in 3,000 ml of toluene and again sedimented in acetone to purify the polymer. The resulting epoxidated EPDM was air dried and then dried in vacuo. There was obtained 120 g of epoxidated EPDM in a yield of 80%.

The epoxy equivalent of the glycidyl-modified EPDM measured in the same way as Application Example 13 was 3,070.

The glycidyl-modified EPDM described above, the aromatic oligomer having a benzoic acid alone at one end of the molecule obtained in Example 19 and triparatolylphosphine used as catalyst were melt mixed at a ratio of glycidyl-modified EPDM/aromatic oligomer/triparatolylphosphine=40 g/10 g/0.05 g by Laboplastomill R-20 (mfd. by Toyo Seiki Seisaku-sho Ltd.) equipped with a R-60 mixer and roller type blades at 230° C. and 200 r.p.m. for 3 minutes. The melt index of the thus obtained graft copolymer at 260° C. and under a load of 10 kg was 0.5 g/10 min.

This graft copolymer was worked into a 2.1 mm thick pressed sheet at 260° C. under a pressure of 50 kg/cm². The test pieces for measuring the various properties were cut out from said sheet and the various properties were measured. The results are shown in Table 6.

APPLICATION EXAMPLE 15

A graft copolymer was obtained in accordance with Application Example 14 except that the glycidyl-modified EPDM/aromatic oligomer/triparatolylphosphine ratio was changed to 40 g/10 g/0.10 g. The obtained graft copolymer was worked into a pressed sheet and its various properties were determined in the same way as Application Example 13. The results are shown in Table 6.

The graft copolymers obtained in Examples 11 to 13 were insoluble in toluene which is a good solvent for EPDM, epoxidated EPDM and glycidyl-modified EPDM used in the present example.

COMPARATIVE APPLICATION EXAMPLE 5

From an ethylene/propylene/dicylclopentadiene terpolymer used in Application Example 13, there was produced a pressed sheet in the same way as Application Example 13. The test pieces for measuring various properties were cut out from said sheet and the properties were determined. The results are shown in Table 6.

APPLICATION EXAMPLES 16-19

An ethylene-methyl acrylate-glycidyl methacrylate terpolymer (ethylene/methyl acrylate/glycidyl methacrylate=35/63/2 (by weight), MI at 190° C. and under a load of 2.16 kg: 8.7 g/10 min) was obtained according to the method described in Japanese Patent Application Kokai (Laid-Open) No. 61-127709, Example 5. This polymer is referred to as EMA-1.

100 parts by weight of EMA-1 and 3 parts by weight of dicumyl peroxide were mixed by a Banbury mixer at 150° C. for 10 minutes to obtain a partially crosslinked sample. This polymer is referred to as EMA-2.

Then an aromatic oligomer having a carboxyl group at one terminal of the molecule was synthesized according to Example 13.

EMA-1, EMA-2, the aromatic oligomer having a carboxyl group at one terminal of the molecule, which were described above, and triphenylphosphine were melt mixed and reacted at the ratios shown in Table 7 (the total amount of said substances used being 50 g) by Laboplastomill ME-15 (mfd. by Toyo Seiki Seisaku-sho Ltd.) equipped with a R-60 mixer and roller type blades, in a nitrogen atmosphere at 280° C. and 120 r.p.m. for 10 minutes to obtain the graft copolymers. The melt indices of the obtained graft copolymers (at 232° C. and under a load of 10 kg) are shown in Table 7.

Each of these graft copolymers was worked into a 2.1 mm thick pressed sheet at 280° C. under a pressure of 50 kg/cm². The test pieces for determining the various properties were cut out from said sheet and the properties were determined. The results are shown in Table 7.

EXAMPLE 20

An aromatic polyester oligomer having at both terminals of its molecule a carboxyl group and a hydroxyl group reactable with glycidyl group and represented by the formula shown below was synthesized in the following way.

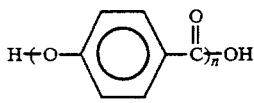

By using the same apparatus as used in Example 13, acetylation, polycondensation and methanol washing were conducted according to the methods of Example 1 except that 1.0 mol (138 g) of p-hydroxybenzoic acid and 0.8 mol (81.6 g) of acetic anhydride were supplied.

The flow temperature of the purified oligomer obtained after methanol washing was 250° C., and the number-average polymerization degree as determined according to GPC described in Example 13 was n=6.3 in the above-shown formula.

Also, said oligomer showed optical anisotropy in the molten state.

APPLICATION EXAMPLES 20-23

EMA-1, the aromatic oligomer having a carboxyl group at one terminal of the molecule, which were described in application Example 16, the aromatic polyester oligomer of Example 20 and triphenylphosphine were melt mixed and reacted at the ratios shown in Table 7 (the total amount of said substances used being 50 g) by Laboplastomill ME-15 (mfd. by Toyo Seiki Seisaku-sho Ltd.) furnished with a R-60 mixer and roller type blades, in a nitrogen atmosphere at 280° C. and 120 r.p.m. for 10 minutes to obtain the graft copolymers. Evaluations of properties of the obtained graft copolymers were made in accordance with Application Example 16. The results are shown in Table 7.

APPLICATION EXAMPLE 24

As the amino-modified organopolysiloxane, Toray Dow-Corning Silicone's BY16-872 (amino equivalent: 2000) having a structure represented by the following formula was used:

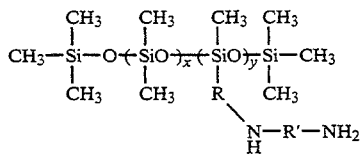

The aromatic oligomer used in Application Example 13 was used as the aromatic oligomer having an acid anhydride group at one terminal of the molecule.

Then, reaction was carried out by using said amino-modified polysiloxane and aromatic oligomer having an acid anhydride group at one terminal of the molecule. 25.0 g of said modified polysiloxane, 9.8 g of said aromatic oligomer, 3.9 mg of lithium chloride and 80 ml of 1-methyl-2-pyrrolidone (NMP) were supplied into a 300 ml separable flask equipped with an anchor shaped agitator, a three-way stop cock and a Dimroth condenser. Nitrogen was introduced through the three-way stop cock and the separable flask was placed in an oil bath so that NMP could be refluxed in the system under a nitrogen stream, and the mixture in the flask was stirred. 3 hours later, the separable flask was taken out of the oil bath and allowed to cool by itself, and then the solvent was decanted. The resultant product was washed twice under methanol refluxing for one hour. After washing, the solution was filtered and the product graft copolymer was recovered. Further, the recovered product was dried at 100° C. by a vacuum dryer to obtain a graft copolymer in which said aromatic oligomer was grafted to said organopolysiloxane.

This graft copolymer was worked into a 2.1 mm thick pressed sheet at 250° C. under a pressure of 50 kg/cm². A test piece for measuring compression set was cut out from said sheet and compression set was measured under the conditions of 70° C. and 22 hours. It was 88.0%. Shore hardness of the test piece was 15. Also, MI of the graft copolymer at 260° C. and under a load of 10 kg was 0.21 g/10 min.

APPLICATION EXAMPLE 25

A modified polysiloxane having hydrogen atom bonded to silicon atom as reactive functional group was synthesized in the following way.

1.48 mol (440 g) of octamethylcyclotetrasiloxane and 0.55 mol (13.2 g) of 1,3,5,7-tetramethylcyclotetrasiloxane purified by distillation from calcium hydride were supplied into a 1,000 ml three-necked flask provided with a Dimroth condenser, a three-way stop cock and a stirrer. Then 3.2 g of trifluoromethanesulfonic acid was added and the mixture was stirred in a nitrogen atmosphere at room temperature. 71 hours later, 8.8 g of sodium hydrogencarbonate was added and the mixture was stirred for 3 hours. Then, after adding hexane, the solids such as unreacted sodium hydrogencarbonate were filtered out from the solution and the solution was dried over anhydrous sodium sulfate. After filtration, the solvent was distilled away and the residue was dried in vacuo at 80° C. The resultantly obtained modified polysiloxane had a number-average molecular weight of 411,635 as determined by GPC. The Si-H equivalent of this polysiloxane as determined by $^1$H-NMR was 2,329.

EXAMPLE 21

A reactive oligomer having an unsaturated double bond at one terminal of the molecule was synthesized in the following way.

0.78 mol (150 g) of trimellitic acid anhydride and 250 ml of 1,4-dioxane distilled from lithium aluminum hydride were supplied, in a nitrogen atmosphere, into a 1,000 ml separable flask equipped with a Dimroth condenser, a dropping funnel and an anchor shaped agitator. Then 0.78 mol (44.6 g) of allylamine was added dropwise from the dropping funnel. After generation of heat has ceased, the mixture was heated at an oil bath temperature of 80° C. for one hour. Then 0.79 mol (80.2 g) of acetic anhydride was added and the mixture was stirred under heating at the refluxing temperature for 2 hours. Thereafter, the solvent was distilled away and 1.2 mol (162 g) of p-hydroxybenzoic acid and 1.3 mol (133 g) of acetic anhydride were added, followed by the same treatments as practiced in the synthesis of the above-described aromatic oligomer to obtain an aromatic oligomer (A) having an unsaturated double bond at one terminal of the molecule:

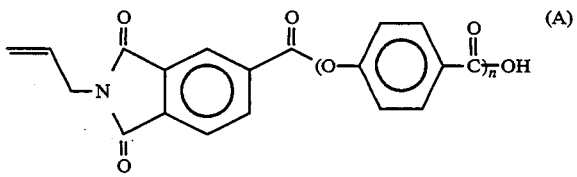

The flow temperature of this oligomer was 162° C. This oligomer showed optical anisotropy when in a molten form.

n was 3.8 as determined by the above-described chemical decomposition method using butylamine.

135 g of said oligomer (A) and 320 g of triphenyl phosphite were supplied, in a nitrogen atmosphere, into a 1,000 ml separable flask furnished with a Dimroth condenser, a three-way stop cock and an anchor shaped agitator, and the mixture was stirred under heating at an oil bath temperature of 200° C. for 6 hours. After allowed to cool by itself, the solution was washed with methanol and dried in vacuo at 80° C. to obtain a phenyl esterified oligomer of the following formula (B):

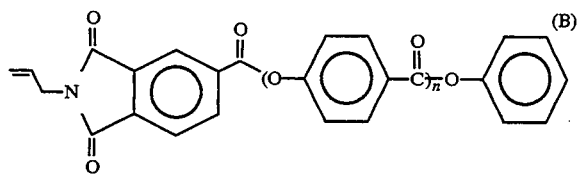

Then, said modified polysiloxane was reacted with the aromatic oligomer (B) having an unsaturated double bond at one terminal of the molecule according to Example 21. 19.1 mg of a 1% platinum/carbon having a water content of 50% was supplied into a 100 ml two-necked flask provided with a three-way stop cock, and the mixture was heated, deaerated and dried, followed by replacement of the intra-system atmosphere with nitrogen. Then 13.0 g of said oligomer (B) was put into the flask, which was then deaerated and subjected to replacement of its atmosphere with nitrogen. 36.2 g of said polysiloxane and the content of the two-necked flask were melt mixed and reacted in Laboplastomill at 200° C. and 200 r.p.m. for one hour to obtain a rubber-like product.

TABLE 1

|  | Theoretical value of number-average polymerization degree of POB oligomer | Number-average degree of polymerization of POB oligomer as determined from the amount of acetic acid released by distillation | Results of measurements | | Flow temperature (°C.) | Temperature at which oligomer shows optical anisotropy (°C.) |
|---|---|---|---|---|---|---|
|  |  |  | Number-average degree of polymerization | Monomer/dimer weight fraction (%) |  |  |
| Example 1 | 2 | 1.8 | 1.82 | 46.9 | 155 | 176 |
| Example 2 | 3 | 2.6 | 2.69 | 24.0 | 192 | 217 |
| Example 3 | 4 | 3.5 | 3.52 | 19.2 | 228 | 230 |
| Example 4 | 5 | 4.3 | 4.36 | 13.1 | 250 | 254 |
| Example 5 | 6 | 5.3 | 5.32 | 11.9 | 279 | 283 |
| Example 6 | 7 | 6.2 | 6.26 | 9.7 | 288 | 298 |
| Example 7 | 8 | 7.1 | 7.18 | 9.2 | 301 | 309 |
| Example 8 | 9 | 8.0 | 8.55 | 8.1 | 315 | 324 |
| Comp. Example 1 | 12 | 10.6 | Not measured |  | Unable to flow | No optical anisotropy observed |

TABLE 2

|  | Monomer/dimer weight fraction (%) | Number-average degree of polymerization | Flow temperature (°C.) | Temperature at which oligomer shows optical anisotropy (°C.) |
|---|---|---|---|---|
| Example 9 | 1.4 | 5.8 | 258 | 280 |
| Example 10 | 1.3 | 3.5 | 181 | 187 |
| Example 11 | 0.5 | 4.5 | 210 | 225 |
| Example 12 | 0.7 | 5.8 | 242 | 249 |

TABLE 3

|  | Polyethylene terephthalate (parts by weight) | Glass fiber (parts by weight) | Oligomer (parts by weight) | Thin-wall fluidity | | Properties of molded products | | | |
|---|---|---|---|---|---|---|---|---|---|
|  |  |  |  | 340° C. (mm) | 360° C. (mm) | Bending strength (kg/cm$^2$) | Bending modulus (kg/cm$^2$) | Izod impact strength (kg cm/cm) | Thermal deformation strength (°C.) |
| Application Example 1 | 100 | 67 | 3 | 22.5 | 28.9 | 1,510 | 131,000 | 36 | 275 |

TABLE 3-continued

| | Polyethylene terephthalate (parts by weight) | Glass fiber (parts by weight) | Oligomer (parts by weight) | Thin-wall fluidity 340° C. (mm) | Thin-wall fluidity 360° C. (mm) | Properties of molded products Bending strength (kg/cm²) | Bending modulus (kg/cm²) | Izod impact strength (kg cm/cm) | Thermal deformation strength (°C.) |
|---|---|---|---|---|---|---|---|---|---|
| Comp. Application Example 2 | 100 | 67 | — | 15.4 | 21.8 | 1,460 | 131,000 | 39 | 276 |

TABLE 4

| | | Unit | Application Example 4 | Application Example 5 | Application Example 6 | Application Example 7 | Application Example 8 | Comp. Application Example 4 |
|---|---|---|---|---|---|---|---|---|
| Composition | *1 | Parts by weight | 90 | 95 | 80 | 70 | 90 | 100 |
| | *2 | " | 10 | 5 | 20 | 30 | 10 | 0 |
| | Triphenylphosphine | " | 0.1 | 0.05 | 0.2 | 0.2 | 0.1 | 0 |
| Graft efficiency | *3 $G_1$ | % | 67 | 89 | 35 | 20 | — | — |
| | *3 $G_2$ | % | 84 | 53 | 98 | 97 | — | — |
| Tensile test | 100% modulus | kg/cm² | 6.5 | 3.4 | 7.1 | 10.9 | 7.1 | 1.8 |
| | Elongation at break | % | >600 | >600 | >600 | >600 | >600 | >600 |
| | Permanent set | % | 20.0 | 14.0 | 40.0 | 50.0 | 18.0 | 90 |
| Compression set | 70° C., 22 hr. | % | 68.6 | 75.1 | 77.7 | 72.0 | — | 100 |
| | 100° C., 70 hr. | % | 70.1 | 76.5 | 82.8 | 70.0 | — | — |
| | 150° C., 22 hr. | % | 72.5 | 80.7 | 81.4 | 64.2 | — | — |
| | 180° C., 22 hr. | % | — | — | — | — | 45.0 | — |
| Shore hardness | | Shore A | 22 | 18 | 23 | 25 | 20 | 13 |

*1: ethylene-methyl acrylate-glycidyl methacrylate terpolymer described in Application Example 4
*2: Aromatic oligomer having carboxyl group at one terminal of the molecule described in Example 13
*3: graft efficiency determined by the method described in Application Example 4

TABLE 5

| | | | Application Example 9 | | Application Example 10 |
|---|---|---|---|---|---|
| Molding method | | Unit | Press molding | Injection molding | Press molding |
| Graft efficiency | $G_1$ | % | 75 | — | 80 |
| | $G_2$ | % | 85 | — | 89 |
| Tensile test | 100% modulus | kg/cm² | 6.3 | 11.2 | 3.7 |
| | Elongation at break | % | 700 | 475 | 1200 |
| | Breaking strength | kg/cm² | 36.7 | 25.3 | 25.0 |
| | Permanent set | % | 20.0 | 10.0 | 40.0 |
| Compression set | 100° C., 70 hr. | % | 60.0 | 45.4 | 72.8 |
| | 25° C., 22 hr. | % | — | 38.2 | — |
| | 70° C., 22 hr. | % | — | 51.2 | — |
| | 100° C., 22 hr. | % | — | 42.1 | — |
| | 130° C., 22 hr. | % | — | 31.1 | — |
| | 160° C., 22 hr. | % | — | 47.8 | — |
| | 180° C., 22 hr. | % | — | 66.3 | — |
| | 200° C., 22 hr. | % | — | 94.7 | — |
| | Shore hardness | Shore A | 22 | 23 | 13 |

TABLE 6

| | | Application Example 13 | Application Example 14 | Application Example 15 | Comparative Application Example 5 |
|---|---|---|---|---|---|
| Compression set*1 (%) | | 72.8 | 66.8 | 78.4 | 95.0 |
| MI. (g/10 min) | | 3.0*2 | 0.5*2 | 1.31*2 | 3.39*3 |
| Tensile test | 100% modulus (kg/cm²) | 9.87 | 8.26 | 7.70 | 4.35 |
| | Permanent set (%) | 10 | 20 | 20 | 130 |
| | Elongation at break (%) | 250 | 200 | 400 | 1200 |
| | Breaking strength (kg/cm²) | 11.5 | 8.30 | 7.90 | 4.10 |
| | Hardness (Shore A) | 36 | 22 | 23 | 11 |

Measuring conditions for *1: 70° C. and 22 hours
Measuring conditions for *2: 260° C. and 10 kg
Measuring conditions for *3: 230° C. and 2.16 kg

TABLE 7

| | | Unit | Application Example 16 | Application Example 17 | Application Example 18 | Application Example 19 | Application Example 20 | Application Example 21 | Application Example 22 | Application Example 23 |
|---|---|---|---|---|---|---|---|---|---|---|
| Composition | EMA-1 | parts by weight | 50 | 0 | 60 | 40 | 90 | 90 | 95 | 95 |
| | EMA-2 | parts by weight | 40 | 90 | 35 | 40 | — | — | — | — |
| | *1 | parts by weight | 10 | 10 | 5 | 20 | 10 | 10 | 5 | 5 |
| | *1 | parts by weight | — | — | — | — | 0.10 | 0.40 | 0.10 | 0.20 |
| | Triphenylphosphine | parts by weight | 0.1 | 0.1 | 0.1 | 0.1 | 0.1 | 0.1 | 0.1 | 0.1 |
| Tensile test | 100% modulus | kg/cm$^2$ | 4.5 | 4.9 | 3.2 | 8.2 | 4.4 | 4.3 | 3.2 | 3.3 |
| | Elongation at break | % | >600 | >600 | >600 | >600 | >600 | >600 | >600 | >600 |
| | Permanent set | % | 23 | 14 | 25 | 25 | 21 | 18 | 20 | 15 |
| Melt index (232° C., 10 kg load) | | g/10 min | 2.6 | 1.0 | 4.1 | 2.5 | 3.8 | 3.5 | 4.2 | 4.0 |
| Shore hardness | | Shore A | 23 | 24 | 16 | 25 | 23 | 22 | 15 | 17 |
| Compression set | 70° C., 22 hr. | % | 38.2 | 39.0 | 52.0 | 60.5 | 58.2 | 55.0 | 51.3 | 50.1 |
| | 100° C., 70 hr. | % | 40.0 | 40.5 | 58.1 | 62.3 | 61.3 | 57.1 | 55.6 | 51.3 |
| | 150° C., 22 hr. | % | 45.0 | 42.0 | 61.3 | 75.0 | 72.1 | 60.3 | 61.2 | 59.8 |
| | 180° C., 22 hr. | % | 71.0 | 74.0 | 78.2 | 80.1 | 89.0 | 83.1 | 85.1 | 85.3 |

*1: aromatic oligomer having carboxyl group at one terminal of the molecule shown in Example 13
*2: aromatic polyester oligomer shown in Example 20

We claim:

1. An aromatic oligomer comprising repeating structural units represented by the following formula (I), the sum of the monomer content and the dimer content being not greater than 5 % by weight, said oligomer having a number-average degree of polymerization of 3 to 8 and a flow temperature defined below of 100° to 400° C.:

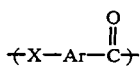

wherein X is selected from O and S, the structural unit containing at least one member selected from the group consisting of O and S; Ar is selected from

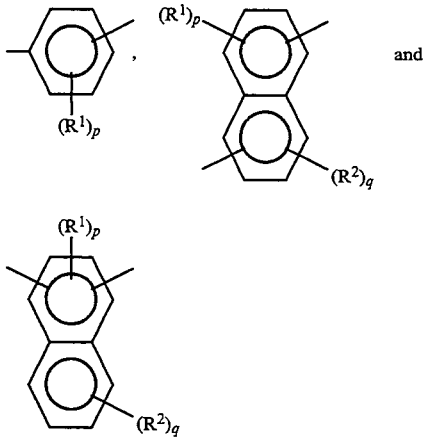

wherein R$^1$ and R$^2$ are each selected from alkyl group having 1-3 carbon atoms and phenyl group; and p and q are each an integer of 0 or 2; and wherein the aromatic oligomer has, at one terminal of the molecule, a functional group selected from the group consisting of a carboxyl group, alkylsilyl ether group, silyl halide group, acid anhydride group and unsaturated double bond flow temperature: the temperature at which the melt viscosity of the oligomer reaches 48,000 poises when the oligomer is melted by heating at a rate of 4° C./min and extruded from a nozzle of 1 mm in inner diameter and 10 mm in length under a load of 100 kg/cm$^2$.

2. An aromatic oligomer according to claim 1, said oligomer showing liquid crystallinity in the melting state at a temperature in the range from 130° to 470° C.

3. A process for preparing an aromatic oligomer according to claim 1, comprising acetylating at least one acid selected from the group consisting of a hydroxyarylcarboxylic acid and a mercaptoarylcarboxylic acid, distilling off acetic acid and conducting an ester exchange reaction in which the at least one acid and an end-termination monomer are reacted.

4. A process for preparing an aromatic oligomer according to claim 1, comprising acetylating at least one acid selected from the group consisting of a hydroxyarylcarboxylic acid and a mercaptoarylcarboxylic acid, distilling off the produced acetic acid and conducting an ester exchange reaction wherein the degree of polymerization of the produced oligomer is calculated by measuring the amount of the acetic acid distilled off, and the ester exchange reaction is terminated when the desired degree of polymerization is reached.

5. A process for preparing an aromatic oligomer according to claim 3, which comprises using as starting materials (a) at least one acid selected from the group consisting of a hydroxyarylcarboxylic acid and a mercaptoarylcarboxylic acid and (b) a carboxylic acid selected from the group consisting of alkylcarboxylic acids, arylcarboxylic acids and aralkylcarboxylic acids having 5 or more carbon atoms, acetylating the at least one acid selected from hydroxyarylcarboxylic acid and mercaptoarylcarboxylic acid with acetic anhydride, then distilling off acetic acid and conducting the ester exchange reaction.

6. A process for preparing an aromatic oligomer according to claim 3, which comprises using as starting materials (a) at least one acid selected from the group consisting of a hydroxyarylcarboxylic acid and a mercaptoarylcarboxylic acid and (b) a compound selected from the group consisting of alkylcarboxylic acids, arylcarboxylic acids and aralkylcarboxylic acids having 5 or more carbon atoms, said compound having at one terminal of the molecule a functional group selected from the group consisting of halogen atom, alkylsilyl ether group, silyl halide group, acid anhydride group and unsaturated double bond, acetylating the hydroxyl groups and mercapto groups of the starting materials with acetic anhydride, then distilling off acetic acid and conducting the ester exchange reaction.

7. A process for preparing an aromatic oligomer according to claim 3, which comprises using as starting materials (a) at least one acid selected from the group consisting of a hydroxyarylcarboxylic acid and a mercaptoarylcarboxylic acid and (b) a compound selected from the group consisting of alkyl alcohols having 5 or more carbon atoms, alkylthiols having 5 or more carbon atoms, arylalcohols, arylthiols, aralkylalcohols and aralkylthiols and having at one terminal of the molecule a functional group selected from the group consisting of halogen atom, alkylsilyl ether group, silyl halide group, acid anhydride group and unsaturated double bond, acetylating the hydroxyl groups and mercapto groups of the starting materials with acetic anhydride, then distilling off acetic acid and conducting the ester exchange reaction.

8. A process for producing an aromatic oligomer according to claim 4, comprising reacting at least one acid selected from the group consisting of a hydroxyarylcarboxylic acid and a mercaptoarylcarboxylic acid with acetic anhydride of a greater number of moles than the total number of moles of said carboxylic acids, acetylating all of the hydroxyl groups and mercapto groups, distilling off acetic acid, conducting the ester exchange reaction and terminating the ester exchange reaction when acetic acid of 1.5 to 1.9 times as much number of moles as the total number of moles of said carboxylic acids has been distilled off.

9. A process for preparing an aromatic oligomer according to claim 3, comprising reacting at least one acid selected from the group consisting of hydroxyarrylcarboxylic acid and a mercaptoarylcarboxylic acid with acetic anhydride of 0.5 to 0.9 times as much number of moles as the total number of moles of said carboxylic acids, acetylating the hydroxyl groups and mercapto groups, distilling off acetic acid and conducting an ester exchange reaction.

* * * * *

UNITED STATES PATENT AND TRADEMARK OFFICE
CERTIFICATE OF CORRECTION

PATENT NO. : 5,446,124
DATED : August 29, 1995
INVENTOR(S) : Masahiro NIWANO et al It is certified that error appears in the above-indentified patent and that said Letters Patent is hereby corrected as shown below:

Title Page, under [30] Foreign Application Priority Data:

"Japan ............ 2-14651"

should read:

-- Japan ........... 2-146511 --

Signed and Sealed this

Twenty-sixth Day of December, 1995

Attest:

BRUCE LEHMAN

Attesting Officer

Commissioner of Patents and Trademarks